US009845509B2

(12) United States Patent
Bungo et al.

(10) Patent No.: US 9,845,509 B2
(45) Date of Patent: Dec. 19, 2017

(54) COMPOSITIONS AND METHODS TO DETECT LEGIONELLA PNEUMOPHILA NUCLEIC ACID

(71) Applicant: Gen-Probe Incorporated, San Diego, CA (US)

(72) Inventors: Jennifer J. Bungo, San Diego, CA (US); James J. Hogan, Coronado, CA (US); Reinhold B. Pollner, San Diego, CA (US); Marie K. Hudspeth, San Diego, CA (US); Shannon K. Kaplan, San Diego, CA (US); Elizabeth M. Marlowe, Encino, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 372 days.

(21) Appl. No.: 14/075,944

(22) Filed: Nov. 8, 2013

(65) Prior Publication Data
US 2014/0113289 A1 Apr. 24, 2014

Related U.S. Application Data

(63) Continuation of application No. 12/624,233, filed on Nov. 23, 2009, now Pat. No. 8,609,829, which is a continuation-in-part of application No. 11/582,770, filed on Oct. 17, 2006, now abandoned.

(60) Provisional application No. 60/727,883, filed on Oct. 17, 2005, provisional application No. 60/735,709, filed on Nov. 9, 2005.

(51) Int. Cl.
*C12Q 1/68* (2006.01)

(52) U.S. Cl.
CPC ............. *C12Q 1/689* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 4,810,644 A | 3/1989 | Tchen et al. | |
| 5,409,818 A | 4/1995 | Davey et al. | |
| 5,491,225 A | 2/1996 | Picone et al. | |
| 5,569,586 A | 10/1996 | Pelletier et al. | |
| 5,677,129 A | 10/1997 | Hogan et al. | |
| 5,703,217 A | 12/1997 | Mabilat et al. | |
| 5,723,344 A | 3/1998 | Mabilat et al. | |
| 5,968,739 A | 10/1999 | Macioszek et al. | |
| 5,969,122 A | 10/1999 | Hammond et al. | |
| 5,976,791 A | 11/1999 | Mabilat et al. | |
| 6,037,122 A | 3/2000 | Mabilat et al. | |
| 6,090,551 A | 7/2000 | Mabilat et al. | |
| 6,150,517 A | 11/2000 | Hogan et al. | |
| 6,194,145 B1 | 2/2001 | Heidrich et al. | |
| 6,251,609 B1 | 6/2001 | Brink et al. | |
| 6,387,652 B1 | 5/2002 | Haugland et al. | |
| 6,830,888 B2 | 12/2004 | Cockerill et al. | |
| 6,844,157 B2 | 1/2005 | Snaidr | |
| 2001/0034048 A1* | 10/2001 | Kurn ................... C12Q 1/6844 435/91.1 |
| 2002/0102571 A1* | 8/2002 | Theaker ............... C12Q 1/6818 435/6.11 |
| 2003/0082577 A1 | 5/2003 | Cockerill et al. | |
| 2003/0194723 A1 | 10/2003 | Cunningham et al. | |
| 2004/0072239 A1 | 4/2004 | Renaud et al. | |
| 2004/0072242 A1 | 4/2004 | Hunter et al. | |
| 2005/0064444 A1 | 3/2005 | Beimfohr et al. | |
| 2007/0184437 A1 | 8/2007 | Breitenstein et al. | |

FOREIGN PATENT DOCUMENTS

| | | | | |
|---|---|---|---|---|
| EP | 0 739 988 A1 | 10/1996 | | |
| FR | 2 811 321 A | 1/2002 | | |
| KR | WO 2006025672 A1 * | 3/2006 | ........... C12Q 1/6837 |
| WO | 94/28174 A | 12/1994 | | |
| WO | 02/10444 A | 2/2002 | | |
| WO | 03/095677 A1 | 11/2003 | | |
| WO | 2005017194 A | 2/2005 | | |
| WO | 2005035789 A | 4/2005 | | |
| WO | 2005049642 A2 | 6/2005 | | |

(Continued)

OTHER PUBLICATIONS

Loens et al. Journal of Microbiological Methods. 2006. 67:408-415.*
GenBank AY298787.*
Deiman et al. Molecular Biotechnology. 2002. 20:163-179.*
Declaration of James J. Hogan. Filed in U.S. Appl. No. 12/624,233, on Jul. 1, 2013.*
Notice of Acceptance, Australia Patent Application No. 2006304721, dated Jan. 4, 2012.
Edelstein, "Evaluation of the Gen-Probe DNA Probe for the Detection of Legionellae in Culture," J. Clin. Microbiol., 1986, 23(3):481-484, ASM, Washington, D.C., USA.
Grimm et al., "Specific Detection of Legionella pneumophila: Construction of a New 16S rRNA-Targeted Oligonucleotide Probe," Appl. Environ. Microbiol., 1998, 64(7):2686-2690, ASM, Washington, D.C., USA.

(Continued)

*Primary Examiner* — Joseph G Dauner
(74) *Attorney, Agent, or Firm* — Jeffrey E. Landes

(57) ABSTRACT

Compositions are disclosed as nucleic acid sequences that may be used as amplification oligomers, including primers, and detection probes that hybridize specifically to *Legionella pneumophila* 23S rRNA sequences or DNA encoding 23S rRNA. Reaction mixtures are disclosed that contain oligonucleotides for the in vitro amplification and/or detection of *Legionella pneumophila* 23S rRNA sequences or DNA encoding 23S rRNA. Methods are disclosed for amplifying and/or detecting the presence of *L. pnuemophila* in samples by using the disclosed compositions in in vitro methods that include nucleic acid amplification and/or detection of a 23S rRNA sequence or DNA encoding the 23S rRNA sequence to produce a detectable amplification product. Reaction mixtures are disclosed that contain oligonucleotides for the in vitro amplification and/or detection of *Legionella pneumophila* 23S rRNA sequences or DNA encoding 23S rRNA.

18 Claims, No Drawings

(56) References Cited

FOREIGN PATENT DOCUMENTS

WO   2007047912 A2   4/2007

OTHER PUBLICATIONS

Jonas et al., "Enzyme-Linked Immunoassay for Detection of PCR-Amplified DNA of Legionellae in Bronchoalveolar Fluid," J. Clin. Microbiol., 1995, 33(5):1247-1252, ASM, Washington, D.C., USA.
Ko et al., "Detection and identification of Legionella pneumophila by PCR-restriction fragment length polymorphism analysis of the RNA polymerase gene (rpoB)," J. Microbiol. Methods, 2003, 54:325-337, Elsevier Science B.V., Amsterdam.
Laussucq et al., "False-Positive DNA Probe Test for Legionella Species Associated with a Cluster of Respiratory Illnesses," J. Clin. Microbiol., 1988, 26(8):1442-1444, ASM, Washington, D.C., USA.
Liu et al., "Use and the dnaJ Gene for the Detection and Identification of All Legionella pneumophila Serogroups and Description of the Primers Used to Detect 16S rDNA Gene Sequences of Major Members of the Genus Legionella," Microbiol. Immunol., 2003, 47(11):859-869, Tokyo Japanese Society for Bacteriology, Tokyo, Japan.
Matsiota-Bernard et al., "Evaluation of Commercial Amplification Kit for Detection of Legionella pneumophila in Clinical Specimens," J. Clin. Microbiol., 1994, 32(6):1503-1505, ASM, Washington, D.C., USA.
Miyamoto et al., "Development of a New Seminested PCR Method for Detection of Legionella Species and its Application to Surveillance of Legionellae in Hospital Cooling Tower Water," Appl. Environ. Microbiol., 1997, 63 (7):2489-2494, ASM, Washington, D.C., USA.
Palmer et al., "Detection of Legionella Species in Reclaimed Water and Air with the EnviroAmp Legionella PCR Kit and Direct Fluorescent Antibody Staining," Appl. Environ. Microbiol., 1995, 61(2):407-412, ASM, Washington, D.C., USA.
Pasculle et al., "Laboratory and Clinical Evaluation of a Commercial DNA Probe for the Detection of Legionella spp.," J. Clin. Microbiol., 1989, 27(10):2350-2358, ASM, Washington, D.C. USA.
Raggam et al., "Qualitative detection of Legionella species in bronchoalveolar lavages and induced sputa by automated DNA extraction and real-time polymerase chain reaction," Med. Microbiol. Immunol., 2002, 191:119-125, Springer-Verlag, Berlin, Germany.
Rantakokko-Jalava et al., "Development of Conventional and Real-Time PCR Assays for Detection of Legionella DNA in Respiratory Specimens," J. Clin. Microbiol., 2001, 39(8):2904-2910, ASM, Washington, D.C., USA.
Stone et al., "Detection of rRNA from four respiratory pathogens using an automated QB replicase assay," Mol. Cell. Probes, 1996, 10:359-370, Academic Press Limited, USA.
Welti et al., "Development of a multiplex real-time quantitative PCR assay to detect Chlamydia pneumoniae, Legionella pneumophila and Mycoplasma pneumoniae in respiratory tract secretions," Diagn. Microbiol. Infect. Dis., 2003, 45:85-95, Elsevier Biomedical, New York, NY.
Wilkinson et al., "Evaluation of a Commercial Gene Probe for Identification of Legionella Cultures," J. Clin. Microbiol., 1986, 23(2):217-220, ASM, Washington, D.C., USA.
Hunter et al., "Haemophilus influenzae 16S rDNA fragment #3," Database accession No. ABL59794 abstract XP-002434811, Jul. 18, 2002, 1 page, Univ. Sydney, AU.
Hunter et al., "Actinobacillus actinomycetemcomitans 16S rDNA fragment #3," Database accession No. ABL59793 abstract XP-002434812, Jul. 18, 2002, 1 page, Univ. Sydney, AU.
Aoki et al., "PCR of blood as the Early Diagnosis of Legionella pneumonia," Abstract #C-455, Abstracts of the 101st General Meeting, May 20-24, 2001, pp. 256-257, vol. 101, American Society for Microbiology, Orlando, FL., US.
Mabilat et al., "PCR Primers A2.1 used to amplify a polymorphic 16S rDNA fragment," Database accession No. ABL41931 abstract XP-002434813, Jun. 11, 2002, 1 page, bioMérieux sa, France.

Mabilat et al., "PCR Primer used to amplify a bacteial 16S rDNA fragment," Database accession No. ABL41941 abstract XP-002434814, Jun. 11, 2002, 1 page, bioMérieux sa, France.
Nakakita Y. et al., "Alicycloibacillus sp. 16S rDNA PCR Primer A1-F3," Database accession No. ADZ45658-abstract XP-002434815, Jun. 30, 2005, 1 page, Sapporo Breweries Limited, Japan.
Marques et al., Legionella pneumophila 16S ribosomal RNA gene, 16S-23S ribosomal RNA intergenic spacer and tRNA-ALA gene, and 23S ribosomal RNA gene, GenBank accession No. AY298787, available at www.ncbi.nlm.nih. gov, 2003, pp. 1-2.
PCT Invitation to Pay Additional Fees, International Application No. PCT/US2006/041017, Jun. 18, 2007.
PCT International Search Report and Written Opinion, International Application No. PCT/US2006/041017, Aug. 28, 2007.
EPO Article 94(3) EPC Communication, European Patent Application No. 06817204.8, Feb. 12, 2009.
USPTO Office Action, U.S. Appl. No. 11/582,770, Jul. 14, 2008.
USPTO Notice of Allowance, U.S. Appl. No. 11/582,770, Aug. 24, 2009.
Crotchfelt, Kimberly A. et al. "Detection of Chlamydia Trachomatis by the Gen-Probe Amplified Chlamydia Trachomatis Assay (AMP CT) in Urine Specimens from Men and Women and Endocervical Specimens from Women." J. Clin. Microbiol. 36(2) (1998): 391-394.
Japanese Office Action translation, Japanese Patent Application No. 2008-536821, May 10, 2011.
Herpers et al. "Real-Time PCR Assay Targets the 23S-5S Spacer for Direct Detection and Differentiation of Legionella ssp. and Legionella pneumophilia." J. Clin. Microbiol. 41(10) (Oct. 1, 2003): 4815-4816.
Nazarian E. J. et al. "A multiplex real-rime PCR assay for the detection of Legionella spp. and Legionella pneumopbila in environmental and clinical samples." Abstracts of the General meeting of the American Society for Microbiology, The Society, Washington, DC, US, vol. 104, Jan. 1, 2004 (Jan. 1, 2001), p. 132.
Extended European Search Report, European Patent Application No. 11006678.4-1222, Nov. 25, 2011.
Requisition by the Examiner, Canadian Patent Application No. 2,625,414, May 4, 2012.
Notice of Reasons for Rejection, Japanese Patent Application No. 2008-536821, dated May 25, 2012.
First Examination Report, European Patent Application No. 11006678.4, dated Oct. 10, 2012.
IPA Examiner's First Report, Australian Patent Application No. 2006304721, Jun. 11, 2010.
Tsourkas et al. "Structure-function relationships of shared-stem and conventional molecular beacons," Nucleic Acids Research, 2002, pp. 4208-4215, vol. 30, No. 19, Oxford University Press, Oxford, UK.
ResSeq Accession AY_298787.1, GI:32481108, NCBI GenBank, Jul. 14, 2003, http://www.ncbi.nlm.nih.gov/nuccore/AY298787.
Buck et al., "Design strategies and performance of custom DNA sequencing primers," Biotechniques, 1999, pp. 528-536, vol. 27, No. 3.
Non-Final Rejection, U.S. Appl. No. 12/624,233, dated Jun. 24, 2011.
Non-Final Rejection, U.S. Appl. No. 121624,233, dated Dec. 9, 2011.
Final Rejection, U.S. Appl. No. 12/624,233, dated Jun. 4, 2012.
Final Rejection, U.S. Appl. No. 12/624,233, dated May 21, 2013.
Notice of Allowance, U.S. Appl. No. 12/624,233, dated Aug. 13, 2013.
International Preliminary Report on Patentability, International Application No. PCT/US2006/041017, dated Apr. 23, 2008.
Requisition by the Examiner, Canadian Patent Application No. 2,625,414, dated Mar. 5, 2013.
Requisition by the Examiner, Canadian Patent Application No. 2,625,414, dated Apr. 26, 2010.
Examiner's Report No. 3, Australia Patent Application No. 2006304721, dated Aug. 29, 2011.

(56) References Cited

OTHER PUBLICATIONS

Examiner's First Report, Australia Patent Application No. 2006304721, dated Jun. 11, 2010.

* cited by examiner

COMPOSITIONS AND METHODS TO DETECT LEGIONELLA PNEUMOPHILA NUCLEIC ACID

RELATED APPLICATIONS

This application is a continuation of application Ser. No. 12/624,233, filed Nov. 23, 2009 and now allowed, which is a continuation-in-part of application Ser. No. 11/582,770, filed Oct. 17, 2006 and which claims the benefit under 35 U.S.C. 119(e) of provisional applications Nos. 60/727,883, filed Oct. 17, 2005, and 60/735,709, filed Nov. 9, 2005, all of which are incorporated by reference.

FIELD OF THE INVENTION

This invention relates to detection of the presence of bacteria in a sample by using molecular biological methods, and specifically relates to detection of *Legionella pneumophila* in a sample by amplifying *L. pneumophila* nucleic acid sequences and detecting the amplified nucleic acid sequences.

BACKGROUND

Legionellae, which consists of the one genus *Legionella*, are fastidious gram-negative bacteria found in moist environments as intracellular parasites of freshwater protozoa (Fields, et al., 2002, Clin. Microbiol. Rev. 15(3): 506-526). Legionellae can multiply in mammalian cells and cause respiratory disease in humans when a susceptible host inhales or aspirates water or an aerosol containing the bacteria. Although at least 48 species of *Legionella* are known, *L. pneumophila* is responsible for most reported cases of legionellosis that result in a severe multisystem disease involving pneumonia, and most other legionellosis cases are caused by *L. bozemanii, L. dumoffli, L. longbeachae*, and *L. micdadei*.

Legionellae may be detected from a number of specimen types and by using a variety of methods. Culture of bacteria from bronchoscopy, bronchoalveolar lavage (BAL), or lung biopsy specimens in a specialized Buffered Charcoal Yeast Extract medium (BCYE) is sensitive and accurate but requires up to two weeks of incubation for maximal recovery followed by identification of the bacteria by using a combination of colony morphology, gram staining, and serologic testing, e.g., immunoassays. Although direct detection of *Legionella* in uncultured clinical specimens is possible by immunofluorescent or radioimmunoassay methods, these tests are often less sensitive. Legionellosis may be diagnosed by indirect detection of a soluble polysaccharide antigen of *L. pneumophila* serogroup 1 in urine, but these assays have limited diagnostic utility because of the time delay needed for seroconversion and cannot detect by used for environmental testing. Molecular diagnostic tests have been developed that use DNA probes or a combination of nucleic acid amplification and DNA probes to detect genetic sequences of Legionellae, including the mip gene of *L. pneumophila*. Such methods detect the presence of nucleic acids from Legionellae in a variety of specimens and with varying degrees of specificity and sensitivity. Many such tests, however, are labor intensive, require at least a day to perform, and are subject to contamination that results in false positive results.

Because Legionellae can survive and persist for a long time in aquatic and moist environments, such as reservoirs and cooling tower water, they can cause community acquired or nosocomial infections. Hence, there is a need for a rapid, sensitive and accurate method to detect Legionellae, particularly *L. pneumophila*, in environmental samples so that an infectious source can be accurately detected and eliminated to prevent infections. There is also a need for methods that allow rapid and accurate detection of *L. pnuemophila* infections in humans so that infected people may be treated promptly to limit morbidity, mortality, and spread of infection.

SUMMARY

Disclosed are methods of detecting *Legionella pneumophila* in a sample, including environmental samples or biological specimens derived from infected humans, by amplifying and detecting target sequences contained in *L. pnuemophila* 16S rRNA or 23S rRNA, of DNA encoding them. By using specific primers and probes disclosed herein, the methods amplify target sequences in 16S and/or 23S rRNA sequences of *L. pneumophila* and detect the amplified products. Some embodiments monitor the development of specific amplification products during the amplification step whereas other embodiments detect the amplification products following the amplification step. Some method embodiments include detection of an internal control or calibrator, e.g., a non-*Legionella* sequence.

A method is disclosed for detecting *L. pnuemophila* in a sample that includes the steps of: providing a sample that contains a *L. pnuemophila* target nucleic acid that is a 16S rRNA sequence or DNA encoding the 16S rRNA sequence, mixing the sample with at least one first amplification oligonucleotide selected from the group consisting of SEQ ID NOS. 30, 31, 32, 33, 34, 35, 36, 37, 40, 41, 42, 43, 44, 45, 53, 54, 60 and 61, combined with at least one second amplification oligonucleotide selected from the group consisting of SEQ ID NOS. 28, 29, 38, 39, 46, 47, 48, 49, 50, 51, 52, 55, 56, 57, 58, and 59, providing an enzyme with nucleic acid polymerase activity and nucleic acid precursors to make an amplification mixture that includes the first and second amplification oligonucleotides and the *L. pneumophila* target nucleic acid, elongating in vitro a 3' end of at least one of the amplification oligonucleotides hybridized to the *L. pnuemophila* target nucleic acid by using the enzyme with nucleic acid polymerase activity and the *L. pneumophila* target nucleic acid as a template to produce an amplified product, and detecting the amplified product to indicate the presence *Legionella pnuemophila* in the sample. In some embodiments, the detecting step hybridizes the amplified product specifically to a detection probe oligomer consisting of SEQ ID NOS. 1, 2, 3, 4, 5, 6, 7, 8, 9, 10, 11, 12, 13, 14, 15, 16, 17, 18, 21, 22, 23, 24, 25, 26, 27, 62, 63, 64, or 65. Some embodiments also include a sample processing step that captures the *L. pneumophila* target nucleic acid from the sample before the hybridizing step, preferably by using a capture probe oligomer that contains a target specific sequence consisting of SEQ ID NO:66, SEQ ID NO:67 or SEQ ID NO:68, which may be covalently attached to a 3' tail sequence. In some embodiments, the mixing step uses a combination of the first and second amplification oligonucleotides selected from the group consisting of: SEQ ID NO:29 with SEQ ID NO:31, SEQ ID NO:28 with SEQ ID NO:31, SEQ ID NO:29 with SEQ ID NO:33, SEQ ID NO:28 with SEQ ID NO:33, SEQ ID NO: 41 with SEQ ID NO:46, SEQ ID NO:41 with SEQ ID NO:55, SEQ ID NO:54 with SEQ ID NO:46, SEQ ID NO:54 with SEQ ID NO:55, SEQ ID NO:51 with SEQ ID NO:43, SEQ ID NO:52 with SEQ ID NO:43, SEQ ID NO:51 with SEQ ID NO:45, SEQ ID NO:52 with SEQ ID NO:45, SEQ ID NO:60 with SEQ ID NO:58 and SEQ ID NO:56, SEQ ID NO:60 with SEQ ID NO:59 and SEQ ID NO:56, SEQ ID NO:60 with SEQ ID NO:58 and SEQ ID NO:57, SEQ ID NO:60 with SEQ ID NO:59 and SEQ ID NO:57, SEQ ID NO:61 with SEQ ID NO:58 and SEQ ID NO:56, SEQ ID NO:61 with SEQ ID NO:59 and SEQ ID NO:56, SEQ ID NO:61 with SEQ ID NO:58 and SEQ ID NO:57, and SEQ ID NO:61 with SEQ ID NO:59 and SEQ ID NO:57. In some preferred embodiments, the mixing step uses a combination of the first and second amplification oligonucleotides selected from the group consisting of: SEQ ID NO:29 with SEQ ID NO:31, SEQ ID NO:28 with SEQ ID NO:31, SEQ ID NO: 41 with SEQ ID NO:46, SEQ ID NO:41 with SEQ ID NO:55, SEQ ID NO:54 with SEQ ID NO:46, SEQ ID NO:54 with SEQ ID NO:55, SEQ ID NO:52 with SEQ ID NO:43, and SEQ ID NO:52 with SEQ ID NO:45.

A composition is disclosed for detecting *Legionella pnuemophila* 16S rRNA sequence or DNA encoding the 16S rRNA sequence by using in vitro amplification, that includes at least one first amplification oligonucleotide selected from the group consisting of SEQ ID NOS. 30, 31, 32, 33, 34, 35, 36, 37, 40, 41, 42, 43, 44, 45, 53, 54, 60 and 61, combined with at least one second amplification oligonucleotide selected from the group consisting of SEQ ID NOS. 28, 29, 38, 39, 46, 47, 48, 49, 50, 51, 52, 55, 56, 57, 58, and 59. The composition may also include at least one capture probe oligomer that contains a target specific sequence consisting of SEQ ID NO:66, SEQ ID NO:67 or SEQ ID NO:68, which is optionally linked with a 3' tail sequence. The composition may also include at least one detection probe oligomer selected from the group consisting of SEQ ID NOS. 1, 2, 3, 4, 5, 6, 7, 8, 9, 10, 11, 12, 13, 14, 15, 16, 17, 18, 21, 22, 23, 24, 25, 26, 27, 62, 63, 64, and 65. Preferred embodiments include at least one detection probe oligomer selected from the group consisting of SEQ ID NOS. 5, 13, 15, and 21. Preferred embodiments of such compositions are provided in the form of a kit., which may optionally include other reagents used in nucleic acid amplification and/or detection.

A method is disclosed for detecting *Legionella pnuemophila* in a sample that includes the steps of providing a sample that contains a *L. pnuemophila* target nucleic acid that is a 23S rRNA sequence or DNA encoding the 23S rRNA sequence, mixing the sample with at least one first amplification oligonucleotide selected from the group consisting of SEQ ID NOS. 69, 70, 71, 74, 75, 76, 77, 78, 79, 80, 81, 82, and 83, combined with at least one second amplification oligonucleotide selected from the group consisting of SEQ ID NOS. 84, 85, 86 and 87, providing an enzyme with nucleic acid polymerase activity and nucleic acid precursors to make an amplification mixture that includes the first and second amplification oligonucleotides and the *L. pneumophila* target nucleic acid, elongating in vitro a 3' end of at least one of the amplification oligonucleotides hybridized to the *L. pnuemophila* target nucleic acid by using the enzyme with nucleic acid polymerase activity and the *L. pneumophila* target nucleic acid as a template to produce an amplified product, and detecting the amplified product to indicate the presence *Legionella pnuemophila* in the sample. In some embodiments, the detecting step hybridizes the amplified product specifically to a detection probe oligomer selected from the group consisting of SEQ ID NOS. 72, 88 and 89. Other embodiments may also include a sample processing step that captures the *L. pneumophila* target nucleic acid from the sample before the hybridizing step, preferably by using a capture probe oligomer that contains a target specific sequence consisting of SEQ ID NO:73, which may be covalently attached to a 3' tail sequence. In some embodiments, the mixing step uses a combination of the first and second amplification oligonucleotides selected from the group consisting of: SEQ ID NO:69 or SEQ ID NO:70 with SEQ ID NO:84, any one of SEQ ID NOS. 71 to 77 with SEQ ID NO:84, SEQ ID NO:78 or SEQ ID NO:79 with SEQ ID NO:84, any one of SEQ ID NOS. 80 to 83 with SEQ ID NO:84, SEQ ID NO:69 or SEQ ID NO:70 with SEQ ID NO:85, any one of SEQ ID NOS. 71 to 77 with SEQ ID NO:85, SEQ ID NO:78 or SEQ ID NO:79 with SEQ ID NO:85, any one of SEQ ID NOS. 80 to 83 with SEQ ID NO:85, SEQ ID NO:69 or SEQ ID NO:70 with SEQ ID NO:86, any one of SEQ ID NOS. 71 to 77 with SEQ ID NO:86, SEQ ID NO:78 or SEQ ID NO:79 with SEQ ID NO:86, any one of SEQ ID NOS. 80 to 83 with SEQ ID NO:86, SEQ ID NO:69 or SEQ ID NO:70 with SEQ ID NO:87, any one of SEQ ID NOS. 71 to 77 with SEQ ID NO:87, SEQ ID NO:78 or SEQ ID NO:79 with SEQ ID NO:87, and any one of SEQ ID NOS. 80 to 83 with SEQ ID NO:87. Preferred embodiments include those in which the mixing step uses a combination of the first and second amplification oligonucleotides selected from the group consisting of: SEQ ID NO:79 with SEQ ID NO:85 and SEQ ID NO:87; SEQ ID NO:75 with SEQ ID NO:84 and SEQ ID NO:87; and SEQ ID NO:75 with SEQ ID NO:85 and SEQ ID NO:87.

A composition is disclosed for detecting a *Legionella pnuemophila* 23S rRNA sequence or DNA encoding the 23S rRNA sequence by using in vitro amplification, that includes at least one first amplification oligonucleotide selected from the group consisting of SEQ ID NOS. 69, 70, 71, 74, 75, 76, 77, 78, 79, 80, 81, 82, and 83, combined with at least one second amplification oligonucleotide selected from the group consisting of SEQ ID NOS. 84, 85, 86 and 87. In preferred embodiments, the composition is a combination of first and second amplification oligonucleotides selected from the group consisting of: SEQ ID NO:79 with SEQ ID NO:85 and SEQ ID NO:87; SEQ ID NO:75 with SEQ ID NO:84 and SEQ ID NO:87; and SEQ ID NO:75 with SEQ ID NO:85 and SEQ ID NO:87. Some embodiments also include at least one capture probe oligomer that contains a target specific sequence consisting of SEQ ID NO:73, which may be covalently attached to a 3' tail sequence. Some embodiments of the composition also include at least one detection probe oligomer selected from the group consisting of SEQ ID NOS. 72, 88 and 89. Preferred embodiments of such compositions are provided in the form of a kit., which may optionally include other reagents used in nucleic acid amplification and/or detection.

DETAILED DESCRIPTION

Methods are disclosed for sensitively and specifically detecting the presence of *L. pneumophila* in an environmental or biological sample by detecting *L. pneumophila* nucleic acids. The methods include performing a nucleic acid amplification of 16S or 23S rRNA sequences and detecting the amplified product, typically by using a nucleic acid probe that specifically hybridizes to the amplified product to provide a signal that indicates the presence of *L. pneumophila* in the sample. The amplification step includes contacting the sample with a one or more amplification oligomers specific for a target sequence in 16S or 23S rRNA to produce an amplified product if *L. pneumophila* rRNA in present in the sample. Amplification synthesizes additional copies of the target sequence or its complement by using at least one nucleic acid polymerase to extend the sequence from an amplification oligomer (a primer) using a *L. pneumophila* template strand. Preferred embodiments for detecting the amplified product use a hybridizing step that includes contacting the amplified product with at least one probe specific for an amplified sequence, e.g., a sequence contained in the target sequence that is flanked by a pair of amplification oligomers. The detecting step may be performed after the amplification reaction is completed, or may be performed simultaneous with the amplification reaction (sometimes referred to as "real time"). In preferred embodiments, the detection step detects the amplified product that uses a probe that is detected in a homogeneous reaction, i.e., detection of the hybridized probe does not require removal of unhybridized probe from the mixture (e.g., U.S. Pat. Nos. 5,639,604 and 5,283,174, Arnold Jr. et al.). In preferred embodiments that detect the amplified product near or at the end of the amplification step, a linear probe hybridizes to the amplified product to provide a signal that indicates hybridization of the probe to the amplified sequence. In preferred embodiments that use real-time detection, the probe is preferably a hairpin structure probe that includes a reporter moiety that provides the detected signal when the probe binds to the amplified product. For example, a hairpin probe may include a reporter moiety or label, such as a fluorophore ("F"), attached to one end of the probe and an interacting compound, such as quencher ("Q"), attached to the other end the hairpin structure to inhibit signal production when the hairpin structure is in the "closed" conformation and not hybridized to the amplified product, whereas a detectable signal results when the probe is hybridized to a complementary sequence in the amplified product, thus converting the probe to a "open" conformation. Examples of hairpin structure probe include a molecular beacon, molecular torch, or hybridization switch probe and other forms (e.g., U.S. Pat. Nos. 5,118,801 and 5,312,728, Lizardi et al., U.S. Pat. Nos. 5,925,517 and 6,150,097, Tyagi et al., U.S. Pat. Nos. 6,849, 412, 6,835,542, 6,534,274, and 6,361,945, Becker et al., U.S. Pat. No. 8,034,554, Becker et al., and US Pub. No. 2006-0194240 A1, To aid in understanding this disclosure, some terms used herein are described below. Unless otherwise described, scientific and technical terms used herein have the same meaning as commonly understood by those skilled in the relevant art based on technical literature, e.g., in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), or *Dorland's Illustrated Medical Dictionary*, 30$^{th}$ ed. (2003, W.B. Saunders, Elsevier Inc., Philadelphia, Pa.). Unless otherwise described, techniques employed or contemplated herein are standard methods well known in the art of molecular biology.

"Sample" includes any specimen that may contain *Legionella* bacteria or components thereof, such as nucleic acids or nucleic acid fragments. Samples may be obtained from environmental sources, e.g., water, soil, slurries, debris, biofilms from containers of aqueous fluids, airborne particles or aerosols, and the like, which may include processed samples, such as those obtained from passing an environmental sample over or through a filters, by centrifugation, or by adherence to a medium, matrix, or support. "Biological samples" include any tissue or material derived from a living or dead mammal, including humans, which may contain Legionellae or target nucleic acid derived therefrom, e.g., respiratory tissue or exudates such as bronchoscopy, bronchoalveolar lavage (BAL) or lung biopsy, sputum, peripheral blood, plasma, serum, lymph node, gastrointestinal tissue, urine, exudates, or other body fluids. A sample may be treated to physically or mechanically disrupt aggregates or cells to release intracellular components, including nucleic acids, into a solution which may contain other components, such as enzymes, buffers, salts, detergents and the like.

"Nucleic acid" refers to a multimeric compound comprising nucleosides or nucleoside analogs which have nitrogenous heterocyclic bases, or base analogs, which are linked by phosphodiester bonds or other linkages to form a polynucleotide. Nucleic acids include RNA, DNA, or chimeric DNA-RNA polymers, and analogs thereof. A nucleic acid "backbone" may be made up of a variety of linkages, including one or more of sugar-phosphodiester linkages, peptide-nucleic acid (PNA) bonds (PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine; *The Biochemistry of the Nucleic Acids* 5-36, Adams et al., ed., 11$^{th}$ ed., 1992), derivatives of purine or pyrimidine bases, e.g., N$^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines, and pyrazolo-compounds, such as unsubstituted or 3-substituted pyrazolo[3,4-d]pyrimidine (U.S. Pat. Nos. 5,378,825, 6,949,367 and PCT No. WO 93/13121). Nucleic acids may include "abasic" positions in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids also include "locked nucleic acids" (LNA), an analogue containing one or more LNA nucleotide monomers with a bicyclic furanose unit locked in an RNA mimicking sugar conformation, which enhances hybridization affinity toward complementary sequences in single-stranded RNA (sRNA), single-stranded DNA (ssDNA), or double-stranded DNA (dsDNA) (Vester et al., 2004, *Biochemistry* 43(42): 13233-41). Methods for synthesizing nucleic acids in vitro are well known in the art.

The interchangeable terms "oligomer" and "oligonucleotide" refer to a nucleic acid having generally less than 1,000 nucleotides (nt), including polymers in a range having a lower limit of about 2 nt to 5 nt and an upper limit of about 500 nt to 900 nt. Preferred oligomers are in a size range having a lower limit of about 5 nt to 15 nt and an upper limit of about 50 nt to 600 nt, and particularly preferred embodiments are in a range having a lower limit of about 10 nt to 20 nt and an upper limit of about 22 nt to 100 nt. Preferred oligomers are synthesized by using any well known enzymatic or chemical method and purified by standard methods, e.g., chromatography.

An "amplification oligomer" is an oligonucleotide that hybridizes to a target nucleic acid, or its complement, and participates in a nucleic acid amplification reaction. An example of an amplification oligomer is a "primer" that hybridizes to a template nucleic acid and contains a 3' hydroxyl end that is extended by a polymerase in an amplification process. Another example is an oligonucleotide that participates in or facilitates amplification but is not extended by a polymerase, e.g., because it has a 3' blocked end. Preferred size ranges for amplification oligomers include those that are about 10 to about 60 nt long and contain at least about 10 contiguous bases, and more preferably at least 12 contiguous bases that are complementary to a region of the target nucleic acid sequence (or its complementary sequence). The contiguous bases are preferably at least 80%, more preferably at least 90%, and most preferably about 100% complementary to the target sequence to which the amplification oligomer binds. An amplification oligomer may optionally include modified nucleotides or analogs, or optionally an additional sequence that participate in an amplification reaction but are not complementary to or contained in or complementary to the target or template sequence. For example, a "promoter primer" is an oligonucleotide that includes a 5' promoter sequence that is non-complementary to the target nucleic acid but is adjacent or near to the target complementary sequence of the primer. Those skilled in the art will understand that an amplification oligomer that functions as a primer may be modified to include a 5' promoter sequence, and thus function as a promoter-primer, and a promoter-primer can function as a primer independent of its promoter sequence, i.e., the oligonucleotide may be modified by removal of, or synthesis without, its promoter sequence. An amplification oligomer referred to as a "promoter provider" includes a promoter sequence that serves as a template for polymerization but the oligonucleotide is not extended from its 3' end which is blocked and, therefore, not available for extension by polymerase activity.

"Amplification" refers to any known in vitro procedure for obtaining multiple copies of a target nucleic acid sequence or fragments thereof, or its complementary sequence. Amplification of "fragments" refers to production of an amplified nucleic acid that contains less than the complete target nucleic acid or its complement, e.g., by using an amplification oligonucleotide that hybridizes to and initiates polymerization from an internal position of the target nucleic acid. Known amplification methods include, for example, replicase-mediated amplification, the polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (e.g., U.S. Pat. No. 4,786,600, Kramer et al.). PCR amplification uses a DNA polymerase, pairs of primers, and thermal cycling to synthesize multiple copies of two complementary strands of a dsDNA or from a cDNA (e.g., U.S. Pat. Nos. 4,683,195, 4,683,202, and 4,800,159, Mullis et al.). LCR amplification uses four or more different oligonucleotides to amplify a target and its complementary strand by using multiple cycles of hybridization, ligation, and denaturation (e.g., U.S. Pat. No. 5,427,930, Birkenmeyer et al., U.S. Pat. No. 5,516,663, Backman et al.). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. No. 5,422,252, Walker et al., U.S. Pat. No. 5,547,861, Nadeau et al., U.S. Pat. No. 5,648,211, Fraiser et al.).

"Transcription-associated amplification" or "transcription-mediated amplification" (TMA) refer to any type of nucleic acid amplification that uses an RNA polymerase to produce multiple RNA transcripts from a nucleic acid template. These methods generally use an RNA polymerase, a DNA polymerase, nucleic acid substrates (dNTPs and rNTPs), and a template complementary oligonucleotide that includes a promoter sequence, and optionally may include one or more other oligonucleotides. Variations of transcription-associated amplification are well known in the art (e.g., disclosed in detail in U.S. Pat. Nos. 5,399,491 and 5,554,516, Kacian et al.; U.S. Pat. No. 5,437,990, Burg et al.; PCT Nos. WO 88/01302 and WO 88/10315, Gingeras et al.; U.S. Pat. No. 5,130,238, Malek et al.; U.S. Pat. Nos. 4,868,105 and 5,124,246, Urdea et al.; PCT No. WO 95/03430, Ryder et al.; and U.S. Pat. No. 7,374,885, Becker et al.). TMA methods of Kacian et al. and a one-primer transcription-associated method (U.S. Pat. No. 7,374,885, Becker et al.) are preferred embodiments of transcription associated amplification methods for use in detection of *Legionella* target sequences as described herein. Although preferred embodiments are illustrated by such amplification reactions, a person of ordinary skill in the art will appreciated that amplification oligomers disclosed herein may be readily used in other amplification methods that extend a sequence from primer(s) by using a polymerase.

"Probe" refers to a nucleic acid oligomer that hybridizes specifically to a target sequence in a nucleic acid, preferably in an amplified nucleic acid, under conditions that allow hybridization to permit detection of the target sequence or amplified nucleic acid. Detection may either be direct (i.e., probe hybridized directly to its target sequence) or indirect (i.e., probe linked to its target via an intermediate molecular structure). A probe's "target sequence" generally refers to a subsequence within a larger sequence (e.g., a subset of an amplified sequence) that hybridizes specifically to at least a portion of a probe by standard base pairing. A probe may include target-specific sequence and other sequences that contribute to the probe's three-dimensional conformation (e.g., described in U.S. Pat. Nos. 5,118,801 and 5,312,728, Lizardi et al.; U.S. Pat. Nos. 6,849,412, 6,835,542, 6,534,274, 6,361,945, and 8,034,554).

By "sufficiently complementary" is meant a contiguous sequence that is capable of hybridizing to another sequence by hydrogen bonding between a series of complementary bases, which may be complementary at each position in the sequence by standard base pairing (e.g., G:C, A:T or A:U pairing) or may contain one or more positions, including abasic ones, which are not complementary bases by standard hydrogen bonding. Contiguous bases are at least 80%, preferably at least 90%, and more preferably about 100% complementary to a sequence to which an oligomer is intended to specifically hybridize. Sequences that are "sufficiently complementary" allow stable hybridization of a nucleic acid oligomer to its target sequence under the selected hybridization conditions, even if the sequences are not completely complementary. Appropriate hybridization conditions are well known in the art, can be predicted readily based on base sequence composition, or can be determined by using routine testing (e.g., Sambrook et al., *Molecular Cloning, A Laboratory Manual*, $2^{nd}$ ed. (Cold Spring Harbor Laboratory Press, Cold Spring Harbor, N.Y., 1989), §§1.90-1.91, 7.37-7.57, 9.47-9.51 and 11.47-11.57, particularly at §§9.50-9.51, 11.12-11.13, 11.45-11.47 and 11.55-11.57).

"Sample preparation" refers to any steps or methods that prepare a sample for subsequent amplification and detection of *Legionella* nucleic acids present in the sample. Sample preparation may include any known method of concentrating components from a larger sample volume or from a substantially aqueous mixture, e.g., by filtration or trapping of airborne particles from an air sample or microbes from a water sample. Sample preparation may include lysis of cellular components and removal of debris, e.g., by filtration or centrifugation, and may include use of nucleic acid oligomers to selectively capture the target nucleic acid from other sample components.

A "capture probe" or "capture oligomer" refers to at least one nucleic acid oligomer that joins a target sequence and an immobilized oligomer by using base pair hybridization to selectively capture the target sequence. A preferred capture probe embodiment includes two binding regions: a target sequence-binding region and an immobilized probe-binding region, usually on the same oligomer, although the two regions may be present on different oligomers joined by one or more linkers. For example, a first oligomer may include the immobilized probe-binding region and a second oligomer may include the target sequence-binding region, and the two different oligomers are joined by a linker that joins the two sequences into a functional unit.

An "immobilized probe" or "immobilized nucleic acid" refers to a nucleic acid that joins, directly or indirectly, a capture oligomer to an immobilized support. A preferred immobilized probe is an oligomer joined to a support that facilitates separation of bound target sequence from unbound material in a sample. Supports may include known materials, such as matrices and particles free in solution, e.g., made up of nitrocellulose, nylon, glass, polyacrylate, mixed polymers, polystyrene, silane, polypropylene, metal and preferred embodiments are magnetically attractable particles. Preferred supports are monodisperse magnetic spheres (e.g., uniform size±5%), to which an immobilized probe is joined directly (via covalent linkage, chelation, or ionic interaction), or indirectly (via one or more linkers), where the linkage or interaction between the probe ans support is stable during hybridization conditions.

"Separating" or "purifying" means that one or more components of a mixture, such as a sample, are removed or separated from one or more other components. Sample components include target nucleic acids in a generally aqueous mixture (solution phase) which may include cellular fragments, proteins, carbohydrates, lipids, and other nucleic acids. Separating or purifying removes at least 70%, preferably at least 80%, and more preferably about 95% of the target nucleic acid from other mixture components.

A "label" refers to a molecular moiety or compound that is detected or leads to a detectable signal. A label may be joined directly or indirectly to a nucleic acid probe. Direct labeling can occur through bonds or interactions that link the label to the probe, including covalent bonds or non-covalent interactions, e.g. hydrogen bonds, hydrophobic and ionic interactions, or formation of chelates or coordination complexes. Indirect labeling can occur through use of a bridging moiety or linker (e.g., antibody or additional oligomer), which is either directly or indirectly labeled, and which may amplify the detectable signal. Labels include any detectable moiety, such as a radionuclide, ligand (e.g., biotin, avidin), enzyme, enzyme substrate, reactive group, chromophore (e.g., dye, particle, or bead that imparts detectable color), luminescent compound (e.g., bioluminescent, phosphorescent, or chemiluminescent labels), or fluorophore. Preferred labels include a "homogeneous detectable label" that provides a detectable signal in a homogeneous reaction in which bound labeled probe in a mixture exhibits a detectable change that differs from that of unbound labeled probe, e.g., stability or differential degradation (e.g., U.S. Pat. No. 5,283,174, Arnold et al.; U.S. Pat. No. 5,656,207, Woodhead et al.; U.S. Pat. No. 5,658,737, Nelson et al.). Preferred labels include chemiluminescent compounds, preferably acridinium ester ("AE") compounds that include standard AE and derivatives thereof (described in U.S. Pat. Nos. 5,656,207, 5,658,737 and 5,639,604). Methods of synthesis and attaching labels to nucleic acids and detecting signals from labels are well known (e.g., Sambrook et al., *Molecular Cloning, A Laboratory Manual,* 2nd ed. (Cold Spring Harbor Laboratory Press, Cold Spring Harbor, N.Y., 1989), Chpt. 10; U.S. Pat. Nos. 5,658,737, 5,656,207, 5,547,842, 5,283,174, and 4,581,333).

Methods are disclosed for amplifying and detecting *Legionella* nucleic acid, specifically *L. pneumophila* 16S and 23S rRNA sequences or DNA encoding 16S and 23S rRNA. Disclosed are selected oligonucleotide sequences that specifically recognize target sequences of *L. pneumophila* 16S and 23S rRNA or their complementary sequences, or DNA encoding 16S and 23S rRNA. Such oligonucleotides may function as amplification oligomers, e.g., as primers, promoter primers, blocked oligomers, and promoter provider oligomers, whose functions are known (e.g., described in U.S. Pat. Nos. 4,683,195, 4,683,202, 4,800,159, 5,399,491, 5,554,516 and 5,824,518, and US 2006-0046265 A1). Other embodiments may function as probes to detect the amplified *L. pneumophila* sequences.

Amplification methods that use transcription mediated amplification (TMA) include the steps summarized herein (described in detail in U.S. Pat. Nos. 5,399,491, 5,554,516 and 5,824,518). The target nucleic acid that contains the sequence to be amplified is provided as single stranded nucleic acid (e.g., ssRNA or ssDNA) or made single stranded by conventional methods, e.g., temperature and/or chemical melting of double stranded nucleic acid to provide a single-stranded target nucleic acid. A promoter primer binds specifically its target sequence in the target nucleic acid and an enzyme with reverse transcriptase (RT) activity extends the 3' end of the promoter primer using the target strand as a template, to make a cDNA of the target sequence, which is in an RNA:DNA duplex. Enzymatic RNase activity (e.g., RNaseH) digests the RNA strand of the RNA:DNA duplex and a second primer binds specifically to its target sequence on the cDNA strand downstream from the promoter-primer end. The RT synthesizes a new DNA strand by extending the 3' end of the second primer using the first cDNA as a template to make a dsDNA that contains a functional promoter sequence. An RNA polymerase specific for the promoter sequence then initiates transcription to produce multiple RNA transcripts that are, e.g., about 100 to 1000 amplified copies ("amplicons") of the initial target strand in the reaction. Amplification continues when the second primer binds specifically to its target sequence in each amplicon and RT makes a DNA copy from the amplicon RNA template to produce an RNA:DNA duplex. RNase in the reaction digests the amplicon RNA from the RNA:DNA duplex and the promoter primer binds specifically to its complementary sequence in the newly synthesized DNA. The RT extends the 3' end of the promoter primer to create a dsDNA that contains a functional promoter to which the RNA polymerase binds to transcribe additional amplicons that are complementary to the initial target strand. These autocatalytic reactions make more amplicons repeatedly during the complete amplification reaction, resulting in about a billion-fold amplification of the target sequence that was present in the sample. The amplified products may be detected during amplification, i.e., in real-time, or at completion of the amplification reaction by using a probe that binds specifically to a target sequence in the amplified products. Signal detected from the bound probes indicates the presence of the target nucleic acid in the sample.

Another transcription associated amplification method summarized herein uses one primer and one or more additional amplification oligomers to amplify nucleic acids in vitro by making transcripts (amplicons) that indicate the presence of the target nucleic acid in a sample (described in detail in U.S. Pat. No. 7,374,885, Becker et al.). Briefly, this single primer method uses a primer or "priming oligomer", a "promoter provider" oligomer that is modified to prevent synthetic extension from its 3' end (typically, by including a 3'-blocking moiety) and, optionally, a binding molecule (e.g., a 3'-blocked extender oligomer) to terminate elongation of a cDNA from the target strand. This method includes the steps of binding the target RNA that contains the target sequence with a primer and, optionally, a binding molecule. The primer hybridizes to the 3' end of the target strand and enzymatic RT activity initiates primer extension from the 3' end of the primer to produce a cDNA, to make a duplex of the new strand and the target strand (RNA:cDNA duplex). When a binding molecule is included in the reaction, such as a 3' blocked oligomer, it binds to the target strand next to the 5' end of the target sequence to be amplified. When the primer is extended by DNA polymerase activity of RT to produce the cDNA, strand, polymerization stops when the primer extension product reaches the binding molecule on the target strand and, thus, the 3' end of the cDNA is determined by the position of the binding molecule on the target strand, making the 3' end of the cDNA complementary to the 5' end of the target sequence. The RNA:cDNA duplex is separated, e.g., by RNase H degradation of the RNA strand, or by using conventional strand separation methods. Then, the promoter provider oligomer hybridizes to the cDNA strand near its 3' end. The promoter provider oligomer includes a 5' promoter sequence, a 3' region complementary to a sequence in the 3' region of the cDNA, and a modified 3' end that includes a blocking moiety to prevent initiation of DNA synthesis from the 3' end of the promoter provider oligomer. In the duplex made of the promoter provider oligomer and the cDNA strand, the 3'-end of the cDNA is extended by DNA polymerase activity of the RT enzyme, using the promoter oligomer as a template to add a promoter sequence to the cDNA, to make a functional double-stranded promoter. An RNA polymerase specific for the functional promoter sequence then binds to the promoter and transcribes RNA transcripts complementary to the cDNA which are substantially identical to the target region sequence that was amplified from the initial target strand. The amplified RNA transcripts then serve as substrates in the amplification process by binding the primer and serving as a template for further cDNA production. This method ultimately produces many amplicons from the initial target nucleic acid present in the sample, i.e., it makes multiple copies of the target sequence. In embodiments of the method that do not include the binding molecule, the cDNA made from the primer has an indeterminate 3' end, but the other steps proceed as described above.

Detection of the amplified products may be accomplished by a variety of methods. The amplified nucleic acids may be associated with a surface to produce a detectable physical change, such as an electrical signal. Amplified nucleic acids may be concentrated in or on a matrix and detected by detecting a signal from the concentrated nucleic acid or an associated dye (e.g., an intercalating agent such as ethidium bromide or cyber green). Nucleic acids in solution may be detected by detecting an increased dye association in the solution phase. Preferred embodiments detect nucleic acid probes that are complementary to a sequence in the amplified product and form a probe:amplified product complex that provides a detectable signal (e.g., U.S. Pat. Nos. 5,424,413, and 5,451,503, Hogan et al., and U.S. Pat. No. 5,849,481, Urdea et al.). Directly or indirectly labeled probes that specifically associate with the amplified product provide a detectable signal to indicate the presence of the target nucleic acid in the sample. For example, if a sample contains a target nucleic acid that is *L. pneumophila* 16S rRNA, the amplified product contains the target sequence in or a complementary sequence of the *L. pneumophila* 16S rRNA, and the probe binds directly or indirectly to the amplified product's target sequence to produce a signal that indicates the presence of *L. pneumophila* in the sample.

Preferred probe embodiments that hybridize specifically to the amplified product sequences may be oligomers of DNA, RNA, or a mixture of DNA and RNA nucleotides, which may be synthesized with a modified backbone, e.g., a synthetic oligonucleotide that includes one or more 2'-methoxy substituted RNA groups. Probes for detection of amplified *Legionella* rRNA sequences may be unlabeled and detected indirectly (e.g., by binding to of another binding partner that is detected) or may be labeled with a label that results in a detectable signal. Preferred embodiments include label compounds that emit a detectable light signal, e.g., fluorophores or luminescent compounds detected in a homogeneous mixture. A probe may include more than one label and/or more than one type of label, or detection may rely on using a mixture of probes in which each probe is labeled with a compound that produces a detectable signal (e.g., U.S. Pat. Nos. 6,180,340 and 6,350,579). Labels may be attached to a probe by any of a variety of known means, e.g., covalent linkages, chelation, and ionic interactions, but preferred embodiments covalently link the label to the oligonucleotide. Probes may be substantially linear oligonucleotides, i.e., lacking conformations held by intramolecular bonds, or may be include functional conformational structures, i.e., conformations such those found in hairpin structure probes held together by intramolecular hybridization. Preferred embodiments of linear oligomers generally include a chemiluminescent label, preferably an AE compound.

Hairpin probes are preferably labeled with any of a variety of different types of interacting labels, where one interacting member is usually attached to the 5' end of the hairpin probe and the other interacting member is attached to the 3' end of the hairpin probe. Such interacting members, which may be generally referred to as a reporter dye and a quencher, include a luminescent/quencher pair, luminescent/adduct pair, Forrester energy transfer pair, or a dye dimer. A luminescent/quencher pair may be made up of one or more luminescent labels, such as chemiluminescent or fluorescent labels, and one or more quenchers. In preferred embodiments, a hairpin probe is labeled at one end with a fluorescent label ("F") that absorbs light of a particular wavelength or range and emits light another emission wavelength or range and at the other end with a quencher ("Q") that dampens, partially or completely, signal emitted from the excited F when Q is in proximity with the fluorophore. Such a hairpin probe may be referred to as labeled with a fluorescent/quencher (F/Q) pair. Fluorophores are well known compounds that include, e.g., acridine, fluorescein, sulforhodamine 101, rhodamine, 5-(2'-aminoethyl)aminoaphthaline-1-sulfonic acid (EDANS), TEXAS RED®, Eosine, BODIPY® and lucifer yellow (Tyagi et al., *Nature*

*Biotechnology* 16:49-53, 1998). Quenchers are also well known and include, e.g., 4-(4'-dimethyl-amino-phenylaxo) benzoic acid (DABCYL), thallium, cesium, and p-xylene-bis-pyridinium bromide. Different F/Q combinations are well known and many combinations may function together, e.g., DABCYL with fluorescein, rhodamine, or EDANS. Other combinations of labels for hairpin probes include a reporter dye, e.g., FAM™, TET™, JOE™, VIC™ combined with a quencher such as TAMRA™ or a non-fluorescent quencher.

A preferred embodiment of a hairpin probe is a "molecular torch" that detects an amplified product to indicate the presence of a target *Legionella* sequence in a sample after the amplification step. A molecular torch includes: (1) a target detection means that hybridizes to the target sequence, resulting in an open conformation; (2) a torch closing means that hybridizes to the target detecting means in the absence of the target sequence, resulting in a closed conformation; and (3) a joining means that joins the target detection means and the torch closing means (described in detail in U.S. Pat. Nos. 6,849,412, 6,835,542, 6,534,274, and 6,361,945). A torch probe in open conformation results in a detectable signal that indicates the presence of the amplified target sequence, whereas the closed conformation produces an amount of signal that is distinguishable from that of the open conformation indicating that the target sequence is not present. Another preferred hairpin probe embodiment is a "molecular beacon" that includes a label on one arm of the hairpin sequence, a quencher on the other arm, and a loop region joining the two arms (described in detail in U.S. Pat. Nos. 5,118,801 and 5,312,728). Methods for using such hairpin probes are well known in the art.

Oligomers that are not extended by a nucleic acid polymerase include a blocker group that replaces the 3' OH to prevent enzyme-mediated extension of the oligomer in an amplification reaction. Blocked amplification oligomers and/or blocked detection probes present during amplification (for real time detection) preferably lack a 3' OH but include one or more blocking groups located at or near the 3' end. A blocking group is covalently attached to the 3' terminus of the oligonucleotide or is located near the 3' end, preferably within five residues of the 3' end, and is sufficiently large to limit binding of a polymerase to the oligomer. Many different chemical groups may be used as a blocking moiety, e.g., alkyl groups, non-nucleotide linkers, alkane-diol dideoxynucleotides, and cordycepin.

A preferred method for detection of *L. pneumophila* sequences uses a transcription-associated amplification with a hairpin probe, e.g. molecular torch or molecular beacon, because the probe may be added before amplification, and detection is carried out without further addition of reagents. For example, a probe may be designed so that the Tm of the hybridized arms of the hairpin probe (e.g., target binding domain:target closing domain complex of a molecular torch) is higher than the amplification reaction temperature to prevent the probe from prematurely binding to amplified target sequences. After an interval of amplification, the mixture is heated to open the torch probe arms and allow the target binding domain to hybridize to its target sequence in the amplified product. The solution is then cooled to close probes not bound to amplified products, which closes the label/quencher (F/Q) pair, allowing detection of signals from probes hybridized to the amplified target sequences in a homogeneous reaction. For example, the mixture containing the F/Q labeled hairpin probe is irradiated with the appropriate excitation light and the emission signal is measured.

In other embodiments, the hairpin detection probe is designed so that amplified products preferentially hybridize to the target binding domain of the probe during amplification, thereby changing the hairpin from its closed to open conformation as amplification progresses. The amplification reaction mixture is irradiated at intervals during the amplification reaction to detect the emitted signal from the open probes during amplification, i.e., in real time.

Preparation of samples for amplification of *Legionella* sequences may include separating and/or concentrating organisms contained in a sample from other sample components, e.g., filtration of particulate matter from air, water or other types of samples. Sample preparation may also include chemical, mechanical, and/or enzymatic disruption of cells to release intracellular contents, including *Legionella* 16S or 23S rRNA or DNA encoding the 16S or 23S rRNA. Sample preparation may include a step of target capture to specifically or non-specifically separate the target nucleic acids from other sample components. Nonspecific target preparation methods may selectively precipitate nucleic acids from a substantially aqueous mixture, adhere nucleic acids to a support that is washed to remove other sample components, or use other means to physically separate nucleic acids, including *Legionella* nucleic acid, from a mixture that contains other components. Other nonspecific target preparation methods may selectively separate RNA, including *Legionella* 16S or 23S rRNA, from DNA in a sample.

In a preferred embodiment, *Legionella* rRNA or DNA encoding rRNA are selectively separated from other sample components by specifically hybridizing the *Legionella* nucleic acid to a capture oligomer specific for the *Legionella* target sequence to form a target sequence:capture probe complex that is separated from sample components. A preferred embodiment of specific target capture binds the *Legionella* target:capture probe complex to an immobilized probe to form a target:capture probe:immobilized probe complex that is separated from the sample and, optionally, washed to remove non-target sample components. The capture probe includes a sequence that specifically binds to the *Legionella* target sequence in 16S or 23S rRNA or in DNA encoding 16S or 23S rRNA and also includes a specific binding partner that attaches the capture probe with its bound target sequence to a support (e.g., matrix or particle), which facilitates separating the target sequence from the sample components. In a preferred embodiment, the specific binding partner of the capture probe is a 3' tail sequence that is not complementary to the *Legionella* target sequence but that hybridizes to a complementary sequence on an immobilized probe attached to the support. Preferred 3' tail sequences are substantially homopolymeric 10 to 40 nt sequences (e.g., $A_{10}$ to $A_{40}$) that bind to a complementary immobilized sequence (e.g., poly-T) attached to the support. Target capture occurs in a solution phase mixture that contains capture oligomers that hybridize specifically to the *Legionella* target nucleic acid under hybridizing conditions, usually at a temperature higher than the Tm of the tail sequence:immobilized probe sequence duplex. The *Legionella* target:capture probe complex is captured by adjusting the hybridization conditions so that the capture probe tail then hybridizes to the immobilized probe, and the entire complex on the support is separated from the other sample components. The support with the attached complex that includes the *Legionella* target sequence may be washed to further remove other sample components. Preferred supports are particulate, such as paramagnetic beads, so that particles with the complex that includes the captured *Legionella* target sequence may be suspended in a washing solution and retrieved from the washing solution by using magnetic attraction. In other embodiments, the capture probe may bind nonspecifically to nucleic acids in the sample, including the *Legionella* target sequence, and then similar steps of attaching the capture probe:nucleic acid complexes to a support and separating the captured complexes on the support are performed. Whether target capture is specific or non-specific for the *Legionella* target sequence, the captured nucleic acids are then subjected to in vitro amplification specific for the intended *Legionella* target sequence. To limit the number of handling steps, *Legionella* target nucleic acid may be amplified by mixing the *Legionella* target sequence in the captured complex on the support with amplification reagents, or a primer may be included in the target capture reaction mixture, thus allowing the *Legionella* specific primer and target sequences to hybridize during target capture and be separated together from the sample in the captured complex.

Assays for detection of *Legionella* nucleic acid may optionally include a non-*Legionella* internal control (IC) nucleic acid that is amplified and detected in the same assay reaction mixtures by using amplification and detection oligomers specific for the IC sequence. Amplification and detection of a signal from the amplified IC sequence demonstrates that the assay reagents, conditions, and procedural steps were properly used and performed in the assay if no signal is obtained for the intended target *Legionella* nucleic acid (e.g., samples that provide negative results for *L. pneumophila*). The IC may be used as an internal calibrator for the assay when a quantitative result is desired, i.e., the signal obtained from the IC amplification and detection is used to set a parameter used in an algorithm for quantitating the amount of *Legionella* nucleic acid in a sample based on the signal obtained for amplified an *Legionella* target sequence. A preferred IC embodiment is a randomized sequence that has been derived from a naturally occurring source (e.g., an HIV sequence that has been rearranged in a random manner). A preferred IC may be an RNA transcript isolated from a naturally occurring source or synthesized in vitro, such as by making transcripts from a cloned randomized sequence such that the number of copies of IC included in an assay may be accurately determined. The primers and probe for the IC target sequence are designed and synthesized by using any well known method provided that the primers and probe function for amplification of the IC target sequence and detection of the amplified IC sequence using substantially the same assay conditions used to amplify and detect the *Legionella* target sequence and the IC components in the assay do not interfere with those used to amplify and detect the *Legionella* target sequence. In preferred embodiments that include a target capture-based purification step, a target capture probe specific for the IC target is included in the target capture step so that the IC is treated in the same conditions as used for the intended *Legionella* analyte in all of the assay steps.

Amplification and Detection of 16S rRNA Sequences of *L. pneumophila*

For amplification and detection of target sequences in 16S rRNA sequences (which include 16S rRNA and DNA encoding 16S rRNA) of *L. pneumophila*, oligomers were designed that act as amplification oligomers and detection probes by comparing known sequences of 16S rRNA or gene sequences encoding 16S rRNA and selecting sequences that are common to *L. pneumophila* isolates, but preferably are not completely identical to 16S rRNA sequences of other *Legionella* species or other bacteria. Sequence comparisons were conducted by using known 16S rRNA sequences (rRNA or genes) of *Legionella* species (*L. anisa, L. beliardensis, L. briminghamiensis, L. bozemanii, L. brunensis, L. busanensis, L. cherrii, L. cincinatiensis, L. dumoffii, L. erythra, L. feeleii, L. gresilensis, L. gratiana, L. hackeliae, L. jamestowniensis, L. jordansis, L. lyticum, L. longbeachae, L. micdadei, L. moravica, L. oakridgenesis, L. parisiensis, L. pneumophila, L. quateirensis, L. rubrilucens, L. santicrucis, L. sainthelensi, L. shakespearei, L. spiritensis, L. steigerwaltii, L. taurinesis, L. wadsworthii*) and of other bacterial species (*Escherichia coli, Pseudomonas aeruginosa, P. alcaligenes, P. stutzeri, P. putida, P. syringae, Bordetella parapertus, B. bronchiseptica, Corynebacterium xerosis, C. pseudotuberculosis, Klebsiella pneumoniae*, and *Haemophilus influenzae*). Specific oligonucleotide sequences were selected, synthesized in vitro, and the oligonucleotides were characterized by determining their Tm and hybridization characteristics with complementary target sequences (synthetic or purified rRNA sequences from bacteria) by using standard laboratory methods. The selected oligomers were further tested by using different combinations of the amplification oligomers in amplification reactions with templates that were synthetic 16S RNA target sequences or 16S rRNA purified from various *Legionella* species grown in culture, to determine the relative efficiencies of amplification of the target sequences by using the selected amplification oligomers. The efficiencies of different combinations of oligomers were monitored by detecting the amplified products of the amplification reactions, generally by binding a labeled probe oligomer to the amplified products and detecting the relative amount of signal that indicated the amount of amplified product. Generally, for initial testing of amplification efficiency, linear detection probes labeled with an AE compound were hybridized to the amplified products and detected by using a hybridization protection assay (HPA) that selectively degrades the AE label in unhybridized probes and detects the signal from hybridized probes (substantially as described in U.S. Pat. Nos. 5,283,174, 5,656,207, 5,658,737 and 5,824,475).

Preferred embodiments of the selected amplification oligomers for *L. pneumophila* 16S rRNA target sequences are shown in Table 1. Amplification oligomers include those that may function as primers, promoter primers, and/or promoter provider oligomers. For the latter two, promoter sequences are shown in lower case in Table 1. Some oligomer embodiments include only the target-specific sequence of a corresponding promoter primer or promoter provider oligomer, e.g., SEQ ID NO:30 is a target-specific sequence that is identical to the target-specific sequence contained in SEQ ID NO:31, which includes a 5' promoter sequence. Those skilled in the art will appreciate that the target-specific sequences listed in Table 1 may optionally be attached to the 3' end of any known promoter sequence to function as a promoter primer or promoter provider with the appropriate RNA polymerase for the chosen promoter sequence. Preferred embodiments include a promoter sequence specific for the RNA polymerase of bacteriophage T7 (e.g., SEQ ID Nos. 90, 91, or 92). Preferred embodiments of amplification oligomers may include a mixture of DNA and RNA bases, and 2' methoxy RNA groups, e.g., oligomers of SEQ ID Nos. 56 and 57 may include RNA bases and 2' methoxy linkages at the first four positions from the 5' end. Embodiments of amplification oligomers may be modified by synthesizing the oligomer with a 3' blocked to make the oligomer optimal for functioning as a blocking molecule or promoter provider oligomer in a single primer transcription associated amplification reaction. Preferred embodiments of 3' blocked oligomers include those of SEQ ID Nos. 58, 59, 60 and 61 that include a blocked C near or at the 3' end.

TABLE 1

Amplification Oligomers for Amplification of *Legionella* 16S rRNA Target Sequences

| Sequence | SEQ ID NO. |
|---|---|
| GAGAGGGTAGTGGAATTTCCG | 28 |
| GTAGAGATCGGAAGGAACACCAG | 29 |
| TGTTTGCTCCCCACGCTT | 30 |
| aatttaatacgactcactatagggagaTGTTTGCTCCCCACGCTT | 31 |
| CCAGGGTATCTAATCCTGTTTGCTC | 32 |
| aatttaatacgactcactatagggagaCCAGGGTATCTAATCCTGTTTGCTC | 33 |
| CCATGCAGCACCTGTATCAG | 34 |
| aatttaatacgactcactatagggagaCCATGCAGCACCTGTATCAG | 35 |
| GCCATGCAGCACCTGTAT | 36 |
| aatttaatacgactcactatagggagaGCCATGCAGCACCTGTAT | 37 |
| GATTAAAACTCAAAGGAATTGACGGGG | 38 |
| AAGCGGTGGAGCATGTGG | 39 |
| CTACCCTCTCCCATACTCGAG | 40 |
| aatttaatacgactcactatagggagaCTACCCTCTCCCATACTCGAG | 41 |
| GAGTTGCAGACTCCAATCCG | 42 |
| aatttaatacgactcactatagggagaGAGTTGCAGACTCCAATCCG | 43 |
| GAGTCGAGTTGCAGACTCCAATC | 44 |
| aatttaatacgactcactatagggagaGAGTCGAGTTGCAGACTCCAATC | 45 |
| GTAATACGGAGGGTGCGAG | 46 |
| CGCCCTCTGTATCGGCCATTGTAGC | 47 |
| CCAGGTCGCCCCTTCGC | 48 |
| CCAATCCGGACTACGAACGGCTTTTGAGGATTGGCT | 49 |
| CCAATCCGGACTACGACCGACTTTTAAGGATTTGCT | 50 |
| GGATGACGTCAAGTCATCATGG | 51 |
| CTTACGGGTAGGGCTACACACGTG | 52 |
| GCTACACCGGAAATTCCACTAC | 53 |
| aatttaatacgactcactatagggagaGCTACACCGGAAATTCCACTAC | 54 |
| CGAGCGTTAATCGGAATTACTGG | 55 |
| GCUACACCGGAAAUUCCACUAC | 56 |
| CGGAAATTCCACTACCCTCTCC | 57 |
| CUUUACGCCCAGUAAUUCCG | 58 |
| GCUGGCACGCUCCGUAUUAC | 59 |
| aatttaatacgactcactatagggagaCGTAAAGGGTGCGTAGGTGGTTG | 60 |
| aatttaatacgactcactatagggagaCGAGCGTTAATCGGAATTACTGG | 61 |

Preferred embodiments of the selected detection probes for detecting amplified products of 16S rRNA sequences or DNA encoding 16S rRNA are shown in Table 2. Preferred embodiments of linear detection probes are labeled with a chemiluminescent AE compound attached to the probe oligomer via a linker (substantially as described in U.S. Pat. No. 5,585,481, and U.S. Pat. No. 5,639,604, particularly at column 10, line 6 to column 11, line 3, and Example 8). Examples of preferred labeling positions are a central region of the probe oligomer and near a region of A:T base pairing, at a 3' or 5' terminus of the oligomer, and at or near a mismatch site with a known sequence that is not the desired target sequence. Preferred embodiments of such AE-labeled oligomers include those with a linker between: nt 4 and nt 5 of SEQ ID NO:6, nt 5 and nt 6 of SEQ ID Nos. 2 and 14, nt 6 and nt 7 of SEQ ID NO:14, nt 7 and nt 8 of SEQ ID Nos. 7 and 18, nt 8 and nt 9 of SEQ ID Nos. 13 and 14, nt 9 and nt 10 of SEQ ID Nos. 2, 11, 24, 26, and 27, nt 10 and nt 11 of SEQ ID Nos. 4, 12, 15, and 16, nt 11 and nt 12 of SEQ ID NO:25, nt 12 and nt 13 of SEQ ID Nos. 7 and 18, nt 13 and nt 14 of SEQ ID Nos. 7, 10, 17, and 23, nt 14 and nt 15 of SEQ ID Nos. 1, 2, 3, 16, 21, and 22, nt 15 and nt 16 of SEQ ID Nos. 9 and 15, nt 16 and nt 17 of SEQ ID Nos. 5, 8, 13, and 14, nt 17 and nt 18 of SEQ ID NO:11, nt 18 and nt 19 of SEQ ID NO:6, and nt 19 and nt 20 of SEQ ID Nos. 10, 13, and 14. Detection probes may be used with one or more helper probes that are unlabeled and facilitate binding of the labeled detection probe to its target (U.S. Pat. No. 5,030,557, Hogan et al.). Preferred embodiments of helper probes include those of SEQ ID Nos. 19 and 20. Other detection probe embodiments are oligomers that form hairpin configurations by intramolecular hybridization of the probe sequence. Preferred embodiments of hairpin probe oligomers include the molecular torches of SEQ ID Nos. 62, 63, 64, and 65 in Table 2, in which lower case letters are used for the torch closing means that hybridize to the torch's target detecting means (i.e. the target-complementary region) in the absence of the target sequence. The target-complementary regions of SEQ ID Nos. 62, 63, 64, and 65 are provided in Table 2 as SEQ ID Nos. 93, 94, 95 and 96, respectively. Preferred hairpin probe oligomers are synthesized with a fluorescent label attached at one end and a quencher compound attached at the other end of the sequence. Embodiments of hairpin probes may be labeled with a 5' fluorophore and a 3' quencher, e.g., 5' fluorescein label with 3' DABCYL quencher. Some embodiments of hairpin oligomers include a non-nucleotide linker moiety at selected positions within the sequence, e.g., oligomers that include an abasic 9-carbon ("C9") linker located in: SEQ ID NO:62 between nt 5 and nt 6 or nt 20 and nt 21, SEQ ID NO:63 between nt 5 and nt 6 or nt 23 and nt 24, SEQ ID NO:64 between nt 23 and nt 24, and SEQ ID NO:65 between nt 25 and nt 26. Preferred embodiments of detection probe oligomers may also include a mixture of DNA and RNA bases, and 2' methoxy RNA groups. 2' methoxy modified RNA probe oligomers are exemplified by SEQ ID Nos. 14, 62, 63, 64 and 65.

TABLE 2

Probes for Detection of Amplified Sequences of
Legionella 16S rRNA Target Sequences

| Sequence | SEQ ID NO. |
|---|---|
| GTATTAGGCCAGGTAGCCG | 1 |
| CGGCTACCTGGCCTAATAC | 2 |
| TGGCGAAGGCGGCTACCTGG | 3 |
| GAAGGCGGCTACCTGGCCTAATACTG | 4 |
| GGCGGCTACCTGGCCTAATACTGACAC | 5 |
| CTGTAAACGATGTCAACTAGCTGTTGG | 6 |
| CTTACCTACCCTTGACATACAGTG | 7 |
| CAACGCGAAGAACCTTACCTACCCTTGACATAC | 8 |

TABLE 2 -continued

Probes for Detection of Amplified Sequences of
Legionella 16S rRNA Target Sequences

| Sequence | SEQ ID NO. |
|---|---|
| CGAAGAACCTTACCTACCCTTGACATACAGTG | 9 |
| CCTTACCTACCCTTGACATACAGTGAATTTTGCAGAGATG | 10 |
| GCTTAACCTGGGACGGTCAGATAATAC | 11 |
| TTAACCTGGGACGGTCAGATAAT | 12 |
| CCTGGGACGGTCAGATAATACTGGTTG | 13 |
| CCUGGGACGGUCAGAUAAUACUGGUUG | 14 |
| CTGGGACGGTCAGATAATACTGGTTG | 15 |
| TGGGACGGTCAGATAATACTGGTTG | 16 |
| GGGACGGTCAGATAATACTGGTTGAC | 17 |
| GGACGGTCAGATAATACTGGTTG | 18 |
| CTACAATGGCCGATACAGAGGGCGGC | 21 |
| CGTAAAGGGTGCGTAGGTGGTTGATTAAG | 22 |
| GTAAAGGGTGCGTAGGTGGTTGATT | 23 |
| GATTAAGTTATCTGTGAAATTCCTGG | 24 |
| CGCGTAGGAATATGCCTTGAAG | 25 |
| GGCCTGGCGCTTTAAGATTAGC | 26 |
| CGGCUACCUGGCCUAAUAC | 27 |
| ACCAGUAUUAUCUGACCGUCCC | 93 |
| gggACCAGUAUUAUCUGACCGUCCC | 62 |
| CAACCAGUAUUAUCUGACCGUCC | 94 |
| ggacgCAACCAGUAUUAUCUGACCGUCC | 63 |
| CAACCAGUAUUAUCUGACCGUC | 95 |
| cCAACCAGUAUUAUCUGACCGUCgguugg | 64 |
| GUCAACCAGUAUUAUCUGACCGUC | 96 |
| cGUCAACCAGUAUUAUCUGACCGUCgacg | 65 |

Embodiments of capture probe oligomers for use in sample preparation to separate Legionella 16S rRNA target nucleic acids from other sample components include those that contain the target-specific sequences of SEQ ID NO: 66 (GCTGCCGTTCGACTTGCATGTG), SEQ ID NO:67 (ATCGTCGCCTTGGTAGGCCC), and SEQ ID NO:68 (GCCGGTGCTTCTTCTGTGGGTAACG). Preferred embodiments of the capture probes include a 3' tail region covalently attached to the target-specific sequence to serve as a binding partner that binds a hybridization complex made up of the target nucleic acid and the capture probe to an immobilized probe on a support. Preferred embodiments of capture probes that include the target-specific sequences of SEQ ID Nos. 66, 67, and 68, further include 3' tail regions made up of substantially homopolymeric sequences, e.g., a $dT_3A_{30}$ sequence.

Reagents used in target capture, amplification and detection steps described in the examples herein generally include one or more of the following. Sample Transport Solution: 15 mM sodium phosphate monobasic, 15 mM sodium phosphate dibasic, 1 mM EDTA, 1 mM EGTA, and 3% (w/v) lithium lauryl sulfate (LLS), pH 6.7. Lysis buffer: 790 mM HEPES, 230 mM succinic acid, 10% (w/v) LLS, and 680 mM LiOH. Specimen Dilution Buffer: 300 mM HEPES, 3% (w/v) LLS, 44 mM LiCl, 120 mM LiOH, 40 mM EDTA, pH 7.4. Target Capture Reagent: 250 mM HEPES, 310 mM LiOH, 1.88 M LiCl, 100 mM EDTA, pH 6.4, and 250 µg/ml of paramagnetic particles (0.7-1.05µ particles, SERA-MAG™ MG-CM, Seradyn, Inc., Indianapolis, Ind.) with covalently bound $(dT)_{14}$ oligomers. Wash Solution: (for target capture) 10 mM HEPES, 150 mM NaCl, 6.5 mM NaOH, 1 mM EDTA, 0.3% (v/v) ethanol, 0.02% (w/v) methyl paraben, 0.01% (w/v) propyl paraben, and 0.1% (w/v) sodium lauryl sulfate, pH 7.5. Amplification reagent: a concentrated mixture that was mixed with other reaction components (e.g., sample or specimen dilution buffer) to produce a mixture containing 47.6 mM Na-HEPES, 12.5 mM-acetyl-L-cysteine, 2.5% TRITON™ X-100, 54.8 mM KCl, 23 mM $MgCl_2$, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM $Na_2EDTA$, 5% v/v glycerol, 2.9% trehalose, 0.225% ethanol, 0.075% methylparaben, 0.015% propylparaben, and 0.002% Phenol Red, pH 7.5-7.6. Amplification oligomers (primers, promoter primers, blocker oligomers, or promoter provider oligomers), and optionally probes, may be added to the reaction mixture in the amplification reagent or separately. Enzymes in TMA reactions: about 90 U/µl of MMLV reverse transcriptase (MMLV-RT) and about 20 U/µl of T7 RNA polymerase per reaction (1 U of RT incorporates 1 nmol of dTTP in 10 min at 37° C. using 200-400 µM oligo dT-primed polyA template, and 1 U of T7 RNA polymerase incorporates 1 nmol of ATP into RNA in 1 hr at 37° C. using a T7 promoter in a DNA template). Probe Reagent: for AE-labeled detection probes was 100 mM lithium succinate, 0.1% to 3% (w/v) LLS, 10 mM mercaptoethanesulfonate, and optionally 3% (w/v) polyvinylpyrrolidone. Hybridization Reagent: for AE-labeled probe binding to nucleic acid was 100 mM succinic acid, 2% (w/v) LLS, 100 mM LiOH, 15 mM aldrithiol-2, 1.2 M LiCl, 20 mM EDTA, and 3.0% (v/v) ethanol, pH 4.7. Selection Reagent for preferentially hydrolyzing an AE label on unbound detection probes was 600 mM boric acid, 182.5 mM NaOH, 1% (v/v) octoxynol (TRITON® X-100), pH 8.5. Detection Reagents for producing a chemiluminescent response from AE labels comprised Detect Reagent I (1 mM nitric acid and 32 mM $H_2O_2$), and Detect Reagent II (1.5 M NaOH) to neutralize the pH (U.S. Pat. Nos. 5,283,174, 5,656,744, and 5,658,737). All of the reagent addition and mixing steps may be performed manually, or by using a combination of manual and automated steps, or by using a completely automated system. Amplification methods that use TMA use procedures substantially as disclosed in U.S. Pat. Nos. 5,399,491 and 5,554,516. Amplification methods that use single primer transcription associated amplification use procedures substantially as disclosed in U.S. Pat. No. 7,374,885, Becker et al. Use of AE-labeled probes and signal detection to detect hybridization complexes with target sequences use procedures substantially as disclosed in U.S. Pat. Nos. 5,283,174, 5,656,744, and 5,658,737. Methods for using hairpin probes have been disclosed in detail in U.S. Pat. Nos. 6,849,412, 6,835,542, 6,534,274, and 6,361,945.

By using various combinations of these amplification oligomers and AE-labeled detection probes to provide a detectable chemiluminescent signal, *L. pnuemophila* 16S rRNA sequences were specifically detected when the sample contained about 100 copies of the 16S rRNA target sequence. Preferred embodiments of the methods are illustrated in Examples 1 to 4.

EXAMPLE 1

Specific Amplification and Detection of *L. pnuemophila* Target Sequence

Known numbers of in vitro transcripts of 16S rRNA sequences from *L. pneumophila* and *L. wadsworthii* were separately amplified in TMA reactions using the same conditions and combinations of amplification oligomers and the amplified products were detected by using the same probe (SEQ ID NO:13 labeled with AE between nt 16 and 17). Briefly, specimens were prepared by mixing in specimen dilution buffer 100, 1000, 10000, or 100000 copies of *L. pneumophila* or *L. wadsworthii* 16S rRNA in vitro transcripts. Specimens were mixed with amplification reagent and amplification oligomers (combinations of amplification oligomers of SEQ ID Nos. 41 and 46, or 41 and 55, or 54 and 46, or 54 and 55) and amplified in TMA reactions using substantially the procedures described in detail in U.S. Pat. Nos. 5,399,491 and 5,554,516, Kacian et al. Briefly, the reaction mixture (about 0.08 ml) containing amplification reagent, target nucleic acid, and amplification oligomers (15 pmol of each oligomer in a combination per reaction) was mixed, covered with silicon oil (0.2 ml) to prevent evaporation, and incubated for 10 min at 62° C. and then for 5 min at 42° C. Then the enzyme reagent (0.025 ml containing MMLV-RT and T7 RNA polymerase) was added, and the reaction mixtures were incubated for 60 min at 42° C. Following amplification, detection of the amplified products involved mixing the amplification mixture with a labeled detection probe oligomer of SEQ ID NO:13 (0.1 pmol per reaction in 0.1 ml of probe reagent, an amount previously determined to produce a maximum detectable signal in a detection range of about 5,000,000 relative light units ("RLU")) from the hybridized labeled probe). The mixtures of probe and amplified sequences were incubated to allow the detection probe to hybridize to the amplified product and the chemiluminescent signal produced from hybridized probes was detected substantially as described in U.S. Pat. Nos. 5,283,174 and 5,639,604. Briefly, the probe and amplified product mixtures were incubated for 20 min at 62° C., then cooled at room temperature for about 5 min, and selection reagent (0.25 ml) was added, mixed, and incubated 10 min at 62° C. followed by room temperature for 15 min to hydrolyze the label on unbound probes. Chemiluminescent signal from AE on bound probes was produced by adding Detect Reagent I, incubation, and adding Detect Reagent II, and signal (RLU) was measured by using a luminometer (e.g., LEADER®, Gen-Probe Incorporated, San Diego, Calif.). Results of these assays are shown in Table 3 as the average RLU for two assays performed for each of the amplification oligomers combinations. In all cases, negative controls (i.e., reactions performed in the same manner using specimens with 0 copies of target) provided a background signal of between 1996 and 2579 RLU. The results show that the amplification oligomer combinations of SEQ ID NOS. 41 and 46, or 41 and 55, or 46 and 54, or 55 and 54 in a TMA reaction were able to amplify as few as 100 copies of 16S rRNA target sequence from *L. pneumophila*, as detected by the signal from AE-labeled probe of SEQ ID NO:13 hybridized to amplified products. In contrast, using the same conditions and combinations of amplification oligomers and detection probe, produced generally negative results when *L. wadsworthii* 16S rRNA was used. Only reactions that included high copy numbers of *L. wadsworthii* 16S rRNA (10000 to 100000) produced a signal above the background.

TABLE 3

Assays Using 16S rRNA Sequences from *L. pneumophila* and *L. wadsworthii*

| | | Amplification Oligomers (SEQ ID NOS) | | | |
|---|---|---|---|---|---|
| Target Source | Copies | 41 + 46 | 41 + 55 | 54 + 46 | 54 + 55 |
| *L. pnuemophila* | 100 | 69,967 | 399,768 | 1,625,390 | 969,753 |
| *L. pnuemophila* | 1000 | 778,085 | 1,319,282 | 4,769,716 | 3,995,973 |
| *L. pnuemophila* | 10000 | 4,859,408 | 4,681,879 | 4,928,583 | 4,892,200 |
| *L. pnuemophila* | 100000 | 5,057,675 | 4,952,711 | 5,016,147 | 4,812,010 |
| *L. wadsworthii* | 100 | 2,120 | 2,418 | 2,385 | 2,155 |
| *L. wadsworthii* | 1000 | 2,317 | 3,182 | 3,916 | 2,389 |
| *L. wadsworthii* | 10000 | 3,253 | 20,540 | 4,292 | 3,545 |
| *L. wadsworthii* | 100000 | 10,766 | 160,667 | 24,577 | 14,264 |

Similar assays were performed using the amplification oligomer combinations of SEQ ID Nos. 51 and 43, or 52 and 43, or 51 and 45, or 52 and 45 (each primer used at 15 pmol per reaction) and an AE-labeled detection probe of SEQ ID NO:21. TMA amplification and chemiluminescent detection steps were performed substantially as described above, using in vitro transcripts of 16S rRNA sequences of *L. pneumophila* or *L. wasdworthii* as the target nucleic acid, at 10, 100, 1000, 10000, and 100000 copies per reaction. Amplification oligomer combinations of SEQ ID Nos. 52 and 43 reliably detected 10000 and 100000 copies of *L. pneumophila* target (average RLU of 315,437 and 2,206,102, respectively) and did not detect the same number of copies of *L. wasdworthii* target (average RLU of 7,152 and 7,437, respectively). The amplification oligomer combination of SEQ ID Nos. 52 and 45 reliably detected 1000, 10000 and 100000 copies of *L. pneumophila* target (average RLU of 148,869, 874,748, and 4,099,682, respectively) and did not detect the same number of copies of *L. wasdworthii* target (average RLU of 12,045, 7,868, and 20,482, respectively). The other amplification oligomer combinations did not reliably provide a positive signal for the *L. pneumophila* target sequence.

EXAMPLE 2

Specific Amplification and Detection of *L. pnuemophila* Target Sequences

Using the procedures substantially as described in Example 1, similar TMA reactions were performed by using amplification oligomers of SEQ ID Nos. 54 and 55 (15 pmol each per reaction), and an AE-labeled detection probe of SEQ ID NO:13 (100 fmol per reaction), using purified extracts of total RNA from cultured bacteria that were three strains of *L. pneumophila*, other *Legionella* species (*L. longbeachae, L. micdadei, L. spiritensis*, and *L. wadsworthii*), and non-*Legionella* species (*K. pneumoniae, B. parapertussis*, and *B. bronchiseptica*) as the target nucleic acids. Total RNA were purified using standard methods to reversibly bind RNA to a support (e.g., as described by the manufacturer for an AMBION® RNAqueous product) and purified RNA were quantitated by using standard fluorometry methods. Each RNA target was tested individually for each source in assays using 4 replicate samples. Positive controls were amplified using the same conditions but using known amounts of *L. pnuemophila* in vitro transcripts of 16S rRNA sequences, as described in Example 1. Positive controls were assayed using duplicate reactions that detected 100 or more copies per reaction (average RLU detected were: 1,504,998 RLU for 100 copies, 4,754,776 for 1000 copies, 5,136,953 for 10000 copies, and 5,267,713 for 100000 copies). Negative controls were reaction mixtures that contained no target nucleic acid which provided background signals of 2041 and 2095 RLU. The results (average RLU) of these assays for the total RNA from different targets are shown in Table 4. The results show that the method specifically amplifies and detects *L. pnuemophila* 16S rRNA target sequences and does not significantly amplify and/or detect other 16S rRNA sequences from other *Legionella* species or common non-*Legionella* bacteria. The assay detected signal from amplified 16S rRNA target from 10 fg/reaction of *L. pneumophila* purified rRNA, but the same conditions provided negative results when 10 fg/reaction or 100 fg/reaction of purified rRNA were tested from *L. longbeachae, L. micdadei, L. spiritensis, L. wadsworthii, K. pneumoniae, B. parapertussis*, and *B. bronchiseptica* sources.

TABLE 4

Detection Assays Using RNA Isolated from Different Bacterial Sources

| | Amount | |
|---|---|---|
| Target Source | 10 fg per reaction | 100 fg per reaction |
| *L. pneumophila* (strain 1) | 5,074,970 | 5,203,724 |
| *L. pneumophila* (strain 2) | 4,993,084 | 5,257,040 |
| *L. pneumophila* (strain 3) | 5,027,967 | 5,267,307 |
| *L. longbeachae* | 2,752 | 3,453 |
| *L. micdadei* | 1,871 | 2,105 |
| *L. spiritensis* | 1,879 | 1,908 |
| *L. wadsworthii* | 10,939 | 82,230 |
| *K. pneumoniae* | 1,934 | 1,890 |
| *B. parapertussis* | 1,808 | 1,657 |
| *B. bronchiseptica* | 1,914 | 1,767 |

EXAMPLE 3

Amplification and Detection of *L. pneumophila* 16S rRNA Target Sequence

TMA reactions were performed substantially as described in Example 1, but using different amplification oligomer combinations: SEQ ID Nos. 29 and 31, or 28 and 31, or 29 and 33, or 28 and 33 (15 pmol each per reaction), using *L. pneumophila* 16S rRNA in vitro transcripts as the target for amplification. Amplified products were detected substantially as described in Example 1, but using an AE-labeled probe of SEQ ID NO:5. All of the amplification oligomer combinations detected 1000 or more copies of the target nucleic acid, and may have detected fewer copies of the target but the signals were obscured by relatively high background detected in the negative control tests (without added target nucleic acid). Of these combinations, oligomers of SEQ ID Nos. 29 and 31, and SEQ ID Nos. 28 and 31 performed best in the assays that detected *L. pneumophila* 16S rRNA sequences.

EXAMPLE 4

Target Capture, Amplification and Detection of *L. pneumophila* 16S rRNA Sequence This methods presented here included purification of the target nucleic acid from a sample before the amplification step. Target purification was done by using target capture, substantially as described in U.S. Pat. Nos. 6,110,678, 6,280,952, and 6,534,273. Briefly, samples were prepared containing known amounts of 16S rRNA target nucleic acid (in vitro transcripts at 1, 10, 100 and 10000 copies per sample in a total volume of 0.4 ml of sample transport solution), and mixed with a target capture oligomer (2.5 pmol per assay) of SEQ ID NO:66 or SEQ ID NO:67, to which $dT_3A_{30}$ tails had been covalently attached, and magnetic particles with covalently attached polydT oligomers. The mixtures were incubated first for 30 min at 60° C., then for 30 min at room temperature to form hybridization complexes that captured *Legionella* RNA to the particles. Magnetic particles with captured *Legionella* RNA were separated by applying a magnetic field for 10 min to the container exterior, then the solution phase was aspirated away to remove other sample components, and the particles with attached hybridization complexes were washed twice sequentially (each with 1 ml of wash solution at room temperature, aspirating the wash solution away from the magnetized particles). The particles with attached hybridization complexes including the *Legionella* target nucleic acid were suspended in amplification reagent containing amplification oligomers of SEQ ID Nos. 54 and 55 (each at 15 pmol per assay), and TMA reactions were performed substantially as described in Example 1. Then, the amplified products were detected by using an AE-labeled probe of SEQ ID NO:15 (0.1 pmol per assay) and the chemiluminescent signals were detected substantially as described in Example 1. Duplicate samples were prepared and assayed for each condition and the results, reported as average detected RLU, are shown in Table 5. Negative controls were treated identically but contained no target RNA, and provided backgrounds in a range of 1485 to 1640 RLU. The results in Table 5 show that target capture combined with amplification and detection was able to detect as few as one copy of the *Legionella* target per reaction, although results between duplicate samples were more variable for samples with lower copy numbers (1-10 copies) than for samples that contained 100 or more copies.

TABLE 5

Detection of *L. pneumophila* 16S rRNA Following Target Capture and Amplification

| Target Copies in Sample | Target Capture SEQ ID NO: 67 | Target Capture SEQ ID NO: 66 |
|---|---|---|
| 1 | 971,164 | 960,828 |
| 10 | 974,831 | 1,888,180 |
| 100 | 1,108,534 | 1,972,797 |
| 10000 | 1,991,759 | 1,977,446 |

Similar experiments were performed as described above in assays that used the same target capture probe, amplification primers, and detection probe, but using target RNA prepared from cultures of *L. pnuemophila* serotype 1, *L. pnuemophila* serotype 799, *L. longbeacheae*, *E. coli*, *S. pyrogens*, *Enterococcus* sp., *S. agalactiae* and *S. aureus*, as described in Example 2. The results showed that the assay detected specifically *L. pnuemophila* of both serotypes 1 and 799 (4.9–5.3×10⁶ RLU detected), but did not detect positive signals for any of the other target nucleic acids isolated from other bacteria (all less than 10,000 RLU, usually at background level of about 2000 RLU).

Amplification and Detection of 23S rRNA Sequences of *L. pneumophila*

For amplification and detection of sequences found in 23S rRNA sequences (which include 23S rRNA or DNA encoding 23S rRNA) of *L. pneumophila*, oligomers were designed that act as amplification oligomers and detection probes by comparing known sequences of 23S rRNA or gene sequence encoding 23S rRNA and selecting sequences that are common to *L. pneumophila* isolates, but preferably are not completely identical to 23S rRNA sequences of other *Legionella* species or other bacteria. Sequence comparisons were conducted by using known 23S rRNA sequences (RNA or genes) of *Legionella* species (*L. anisa*, *L. briminghamiensis*, *L. bozemanii*, *L. cherrii*, *L. dumoffii*, *L. gormanii*, *L. hackeliae*, *L. israelensis*, *L. jamestowniensis*, *L. jordansis*, *L. longbeachae*, *L. micdadei*, *L. oakridgenesis*, *L. parisiensis*, *L. pneumophila*, *L. rubrilucens*, *L. santicrucis*, *L. sainthelensi*, and *L. wadsworthii*) and of other bacteria (*Acinetobacter calcoeceticus*, *Enterobacter aerogenes*, *E. cloacae*, *E. gergoviae*, *Pseudomonas aeruginosa*, *P. alcaligenes*, *P. cepacia*, *P. fluorescens*, *P. maltophilia*, *P. mirabolis*, *P. vulgaris*, *P. stutzeri*, *Corynebacterium diversus*, *C. pseudotuberculosis*, *Klebsiella pneumoniae*, *K rhinoscleromatis*, *K. oxytoca*, *Salmonella typhimurium*, *S. enteritidis*, *Shigella sonnei*, and *Vibrio parahaemolyticus*). Specific sequences were selected, synthesized in vitro, and the *L. pneumophila* oligomers were characterized to determine their Tm and hybridization characteristics with complementary target sequences (synthetic or purified rRNA from bacteria) by using standard laboratory methods. Selected *L. pneumophila* oligomer sequences were further tested by using different combinations of amplification oligomers in amplification reactions with synthetic 23S RNA target sequences or 23S rRNA purified from various *Legionella* species grown in culture to determine the amplification efficiencies for 23S rRNA target sequences. The relative efficiencies of different amplification oligomer combinations were measured by detecting the amplified products of the reactions by binding a labeled probe to the amplified products and detecting the relative amount of signal that indicated the amount of amplified product. Usually initial testing of amplification efficiency involved detection of the amplified products by using an AE-labeled linear detection probe hybridized to amplified products and detected by using a HPA method that selectively degrades the AE in unhybridized probes and detects signal from hybridized probes (U.S. Pat. Nos. 5,283,174, 5,656,207, 5,658,737 and 5,824,475).

Selected amplification oligomers for 23S rRNA target sequences are shown in Table 6, in which lower case letters are used for the promoter sequences in promoter primer and promoter provider oligomers. Table 6 lists oligomers that consist of target-specific sequences that are identical to those in corresponding promoter primers (e.g., the target-specific sequence of SEQ ID NO:71 is included in the three promoter primers of SEQ ID Nos. 75-77). Those skilled in the art of molecular amplification methods will appreciate that a target-specific sequence may be synthesized with any known promoter sequence attached to the 5' end of the target-specific sequence. Preferred embodiments include a promoter specific for T7 RNA polymerase, as shown in SEQ ID Nos. 90, 91, and 92.

TABLE 6

Amplification Oligomers for 23S rRNA Target Sequences

| Sequence | SEQ ID NO. |
|---|---|
| CACGTGTCCCGGCCTACTTGTTCG | 69 |
| aatttaatacgactcactatagggagaCACGTGTCCCGGCCTACTTGTTCG | 70 |
| CTGAGTAGAACAATTTGGGAAAGTTGGCG | 71 |
| CUGAGUAGAACAAUUUGGGAAAGUUGGCG | 74 |
| aatttaatacgactcactatagggagaCTGAGTAGAACAATTTGGGAAAGTTGGCG | 75 |
| atttaatacgactcactatagggagaCTGAGTAGAACAATTTGGGAAAGTTGGCG | 76 |
| tttaatacgactcactatagggagaCTGAGTAGAACAATTTGGGAAAGTTGGCG | 77 |
| GGGAAAGTTGGCGATAGAGGGTGAAAGCC | 78 |
| aatttaatacgactcactatagggagaGGGAAAGTTGGCGATAGAGGGTGAAAGCC | 79 |
| GGAGCCTGGCGTGATTTATTATTGAACTGAG | 80 |
| aatttaatacgactcactatagggagaGGAGCCTGGCGTGATTTATTATTGAACTGAG | 81 |
| atttaatacgactcactatagggagaGGAGCCTGGCGTGATTTATTATTGAACTGAG | 82 |
| tttaatacgactcactatagggagaGGAGCCTGGCGTGATTTATTATTGAACTGAG | 83 |
| CUCAGUUCAAUAAUAAAUCACG | 84 |
| CUUUCCCAAAUUGUUCUACUCAG | 85 |
| GCUCCUCCCCGUUCGCUC | 86 |
| GGAUUCACGTGTCCCGGCCTACTTG | 87 |

Probes specific for amplified products of 23S rRNA sequences made by using combinations of the amplification oligomers shown in Table 6 include those of SEQ ID NO:72 (CGAAGGUUUGAUGAGGAAC), SEQ ID NO:88 (cCUCAUCAAACCUUCGUAgaggg), and SEQ ID NO:89 (CGUGCCUAGUUCCUCAUCgcacg), in which lower case letters are used for the torch closing means that hybridize to the torch's target detecting means (i.e. the target-complementary region) in the absence of the target sequence. The target-complementary regions of SEQ ID NO:88 and SEQ ID NO:89 are accordingly SEQ ID NO:97 (CCUCAUCAAACCUUCGUA) and SEQ ID NO:98 (CGUGCCUAGUUCCUCAUC), respectively. Preferred embodiments of detection probes of SEQ ID NO:72 are labeled with an AE label attached to the oligomer by a non-nucleotide linker at positions between nucleotides 6 and 7, 8 and 9, or 12 and 13. Preferred embodiments of the probes of SEQ ID Nos. 88 and 89 include a 5' fluorophore (e.g., fluorescein), a 3' quencher (e.g., DABCYL), and an abasic moiety (e.g., C9) between nucleotides 5 and 6. Preferred embodiments of detection probe oligomers may also include a mixture of DNA and RNA bases, and 2' methoxy RNA groups. SEQ ID Nos. 72, 88 and 89 are all 2' methoxy modified RNA probe oligomers.

Embodiments of capture probes for use in sample preparation to separate *Legionella* 23S rRNA target nucleic acids from other sample components include those that contain a target-specific sequence of SEQ ID NO:73 (CCGAGTTCGCCTTTGCATCCTATG) that hybridizes to a 23S rRNA sequence or DNA encoding 23S rRNA. Preferred capture probe embodiments include a 3' tail sequence covalently attached to the target-specific sequence of SEQ ID NO:73, e.g., a $dT_3A_{30}$ linked to the 3' end of SEQ ID NO:73, that functions as a binding partner to bind the hybridization complex made up of the *Legionella* target nucleic acid and the capture probe to an immobilized probe on a support.

Different amplification oligomers combinations were made from those listed in Table 6 and were tested in single primer transcription associated amplifications as described above, using total RNA or 23S rRNA isolated from *L. pneumophila* and other bacteria as target nucleic acid. Amplified products were detected by using hairpin probes (torch or molecular beacon probes) labeled with a fluorophore (5' fluorescein) and 3' quencher (DABCYL), detecting the fluorescence emitted when the probe bound to amplified sequences. Those assays specifically amplified and detected *L. pneumophila* sequences with a sensitivity of $10^{-10}$ M copies per reaction.

EXAMPLE 5

Amplification and Detection of *L. pneumophila* 23S rRNA Target Sequence

Amplification and detection of a *L. pneumophila* 23S rRNA target sequence was demonstrated in real time by using a probe that hybridizes to the amplified product during the amplification reaction. Amplification was performed by using a single primer transcription associated amplification procedure substantially as described in detail in US 2006-0046265 A1, conducted by using some of the selected amplification oligomers. Amplification oligomer combinations tested included (1) primer of SEQ ID NO:87 with promoter provider of SEQ ID NO:79 and blocker oligomer of SEQ ID NO:85, or (2) primer of SEQ ID NO:87 with promoter provider of SEQ ID NO:75 and blocker oligomer of SEQ ID NO:84. Each of the assays was performed in an amplification reaction (0.060 ml total volume) that contained the *L. pneumophila* target RNA and amplification reagents substantially as described for TMA reactions but with a promoter provider oligomer (12 pmol per reaction), a primer oligomer (12 pmol per reaction), and a blocker oligomer (0.8 pmol per reaction) and a hairpin probe (molecular torch) of SEQ ID NO:89. Reaction mixtures containing the amplification oligomers, target and amplification reagents (but not enzymes) were covered to prevent evaporation, incubated 5 min at 95° C., then 2 min at 42° C., then enzymes were added (10 µl vol) and the reactions were mixed and incubated for 30 min at 42° C., measuring fluorescence every 30 sec during the amplification reaction after enzyme addition. Results of these tests showed that both combinations of amplification oligomers performed well and the hairpin probe provided detectable signal generally at by the $15^{th}$ to $25^{th}$ predetermined interval after amplification began. The assays detected 100 or more copies of the target nucleic acid.

Similar tests were performed by using the *L. pneumophila* 23S rRNA target with a combination of a primer oligomer of SEQ ID NO:87, a promoter provider oligomer of SEQ ID NO:75, and a blocker oligomer of either SEQ ID NO:84 or 85. Amplified products were detected by using a hairpin probe of SEQ ID NO:88. Results of these tests showed that the probe of SEQ ID NO:88 detected $10^3$ or more copies of the target nucleic acid.

A preferred combination of amplification oligomers for real time detection of *L. pneumophila* 23S rRNA target determined by these tests included those of SEQ ID Nos. 75, 84 and 87. Preferred methods of amplifying and detecting 23S rRNA of *L. pneumophila* also include a target capture step performed substantially as described above for capture of 16S rRNA of *L. pneumophila*, but using a target capture oligomer specific for 23S rRNA sequences, such as an oligomer that includes SEQ ID NO:73. Preferred methods use a capture probe of SEQ ID NO:73 synthesized with 2' methoxy RNA groups in the target-specific sequence and a covalently linked to 3' tail sequence, e.g., $dT_3A_{30}$. Using these assays, *L. pneumophila* of serogroups 1 to 14 (ATCC accession nos. 33152, 22154, 22155, 33156, 33215, 33823, 35096, 35289, 43283, 43130, 43290, 43736, and 43703) were positively detected when RNA from about $6 \times 10^5$ cells per 0.1 ml were tested, but no cross-reactivity was observed when similar samples were prepared from 14 *Legionella* species (non-*L. pneumophila* species) and 28 non-*Legionellae* bacteria and tested. The tested non-*L. pneumophila* species included *L. feelei, L. longbeachae, L. wadsworthii, L. dumoffii, L. haeckeliae, L. oakridgeensis, L. birminghamensis, L. jamestownensis, L. jordanis, L. rubrilucens, L. micdadei, L. parisiensis, L. gormandii*, and *L. bozemanii*. The tested non-*Legionellae* bacteria included *Pseudomonas putida, P. cepacia, P. stutzeri, P. acidoverans, P. alcaligenes, P. auroginosa, P. medocina, Acinetobacter calcoaceticus, Staphylococcus epidermidis, Klebsiella pneumoniae, Micrococcus catarrhalis, Enterococcus faecalis, Neisseria meningitidis, N. gonoerrhoeae, Escherichia coli, Moraxella ovis, Haemophilus influenzae, H. parainfluenzae, Streptococcus sanguis, S. mutans, S. pyrogen, S. agalactiae, S. pneumoniae, Corynebacterium aquaticum, C. xerosis*, and *C. striatum*.

The invention claimed is:

1. A method for the amplification of *Legionella pneumophila* 23S nucleic acid present in a sample, the method comprising the steps of:
   (A) contacting the sample with a capture probe that hybridizes to a *Legionella pneumophila* 23S target nucleic acid and separating the target nucleic acid away from other components of the sample;

(B) contacting the separated target nucleic acid from step (A) with a set of oligonucleotides, the set of oligonucleotides comprising:

(i) a first amplification oligonucleotide, the base sequence of which consists of SEQ ID NO:87;

(ii) a second amplification oligonucleotide, the base sequence of which consists of SEQ ID NO:71 joined at its 5' end to a promoter sequence; and (iii) a blocker oligonucleotide, the base sequence of which is at least 80% identical to SEQ ID NO:84; and (C) performing a transcription associated amplification reaction to generate amplification product from the target nucleic acid using the set of oligonucleotides.

2. The method of claim 1, wherein the base sequence of the 5' promoter base sequence consists of the base sequence of SEQ ID NO:90.

3. The method of claim 2, wherein the base sequence of the second amplification oligonucleotide consists of SEQ ID NO:75.

4. A reaction mixture for performing the isothermal amplification of a *Legionella pneumophila* 23S nucleic acid, wherein the reaction mixture comprises:

(A) a *Legionella pneumophila* 23S target nucleic acid that has been separated from components of a biological sample derived from a human;

(B) a first amplification oligonucleotide, the base sequence of which consists of SEQ ID NO:87;

(C) a second amplification oligonucleotide, the base sequence of which consists of SEQ ID NO:71 joined at its 5' end to SEQ ID NO:90; and (D) a blocker oligonucleotide, the base sequence of which is at least 80% identical to SEQ ID NO:84.

5. The reaction mixture of claim 4, wherein that base sequence of the second amplification oligonucleotide consists of SEQ ID NO:75.

6. A method for the detection of *Legionella pneumophila* 23S nucleic acid present in a sample, the method comprising the steps of:

(A) providing a sample suspected of containing *Legionella pneumophila* 23S target nucleic acid;

(B) contacting the sample from step (A) with a set of oligonucleotides, the set of oligonucleotides comprising (i) a first amplification oligonucleotide, the base sequence of which consists of SEQ ID NO:87, (ii) a second amplification oligonucleotide, the base sequence of which consists of SEQ ID NO:71 joined at its 5' end to a promoter sequence, and (iii)a blocker oligonucleotide, the base sequence of which is at least 80% identical to SEQ ID NO:84;

(C) performing a transcription associated amplification reaction to generate amplification product from the target nucleic acid using the set of oligonucleotides; and (D) detecting the amplification product in real time by specifically hybridizing the amplification product with a hairpin detection probe under conditions that allow hybridization, the base sequence of which consists of (i) a target specific sequence that specifically hybridizes to an amplification product target sequence selected from the group consisting of SEQ ID NO:97, SEQ ID NO:98, and the complement of SEQ ID NO:97 or 98, and (ii) a closing sequence, wherein detection of the amplification product indicates the presence of *Legionella pneumophila* in the sample.

7. The method of claim 6, wherein the 5' promoter sequence consists of the base sequence of SEQ ID NO:90.

8. The method of claim 6, wherein the target specific sequence and the closing sequence are a sequence selected from the group consisting of SEQ ID NO:88, SEQ ID NO:89, and the complement of SEQ ID NO:88 or 89.

9. The method of claim 8, wherein the hairpin detection probe further comprises at least one label selected from the group consisting of: a fluorescent label, a quencher label, a chemiluminescent label, a fluorescein label, a DABCYL label and combinations thereof.

10. The method of claim 8, wherein the hairpin detection probe further comprises a label pair selected from the group consisting of: a F/Q pair, a F/DABCYL pair, a fluorescein/Q pair, a luminescent/adduct pair, a Forrester energy transfer pair, and a fluorescein/DABCYL pair.

11. The method of claim 10, wherein one member of the pair is attached to the 5' end of the hairpin detection probe and another member is attached to the 3' end of the hairpin detection probe.

12. The method of claim 6 wherein the hairpin detection probe further comprises a label pair selected from the group consisting of: a F/Q pair, a F/DABCYL pair, a fluorescein/Q pair, a luminescent/adduct pair, a Forrester energy transfer pair, and a fluorescein/DABCYL pair.

13. The method of claim 12, wherein one member of the pair is attached to the 5' end of the hairpin detection probe and another member is attached to the 3' end of the hairpin detection probe.

14. The method of claim 6, wherein the hairpin detection probe base sequence contains one or more substituted sugar moiety selected from the group consisting of 2' methoxy substitutions and 2' halide substitutions.

15. The method of claim 14, wherein the hairpin detection probe further comprises at least one label selected from the group consisting of: a fluorescent label, a quencher label, a chemiluminescent label, a fluorescein label, a DABCYL label and combinations thereof.

16. The method of claim 14, wherein the hairpin detection probe further comprises a label pair selected from the group consisting of: a F/Q pair, a F/DABCYL pair, a fluorescein/Q pair, a luminescent/adduct pair, a Forrester energy transfer pair, and a fluorescein/DABCYL pair.

17. The method of claim 16, wherein one member of the pair is attached to the 5' end of the hairpin detection probe and the other member is attached to the 3' end of the hairpin detection probe.

18. The method of claim 6, wherein the base sequence of the second amplification oligonucleotide consists of the base sequence of SEQ ID NO:75; and the base sequence of the hairpin detection probe consists of the base sequence of SEQ ID NO:88 or the base sequence of SEQ ID NO:89.

* * * * *

SEQUENCE LISTING

```
<160> NUMBER OF SEQ ID NOS: 98

<210> SEQ ID NO 1
<211> LENGTH: 19
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 1
gtattaggcc aggtagccg                                                19

<210> SEQ ID NO 2
<211> LENGTH: 19
<212> TYPE: DNA
<213> ORGANISM: ARTIFICIAL
<220> FEATURE:
<223> OTHER INFORMATION: Synthetic oligomer for 16S rRNA sequence of
      Legionella sp.

<400> SEQUENCE: 2
cggctacctg gcctaatac                                                19

<210> SEQ ID NO 3
<211> LENGTH: 20
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 3
```

```
tggcgaaggc ggctacctgg                                                   20
```

<210> SEQ ID NO 4
<211> LENGTH: 26
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 4

```
gaaggcggct acctggccta atactg                                            26
```

<210> SEQ ID NO 5
<211> LENGTH: 27
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 5

```
ggcggctacc tggcctaata ctgacac                                           27
```

<210> SEQ ID NO 6
<211> LENGTH: 27
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 6

```
ctgtaaacga tgtcaactag ctgttgg                                           27
```

<210> SEQ ID NO 7
<211> LENGTH: 24
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 7

```
cttacctacc cttgacatac agtg                                              24
```

<210> SEQ ID NO 8
<211> LENGTH: 33
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 8

```
caacgcgaag aaccttacct acccttgaca tac                                    33
```

<210> SEQ ID NO 9
<211> LENGTH: 32
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 9

```
cgaagaacct tacctaccct tgacatacag tg                                     32
```

```
<210> SEQ ID NO 10
<211> LENGTH: 40
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 10
ccttacctac ccttgacata cagtgaattt tgcagagatg                        40

<210> SEQ ID NO 11
<211> LENGTH: 27
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 11
gcttaacctg ggacggtcag ataatac                                      27

<210> SEQ ID NO 12
<211> LENGTH: 23
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 12
ttaacctggg acggtcagat aat                                          23

<210> SEQ ID NO 13
<211> LENGTH: 27
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 13
cctgggacgg tcagataata ctggttg                                      27

<210> SEQ ID NO 14
<211> LENGTH: 27
<212> TYPE: RNA
<213> ORGANISM: Artificial
<220> FEATURE:
<223> OTHER INFORMATION: Synthetic oligomer for L. pneumophila 16S rRNA
      sequence
<220> FEATURE:
<221> NAME/KEY: misc_feature
<222> LOCATION: (1)..(27)
<223> OTHER INFORMATION: 2' methoxy RNA nucleotides

<400> SEQUENCE: 14
ccugggacgg ucagauaaua cugguug                                      27

<210> SEQ ID NO 15
<211> LENGTH: 26
<212> TYPE: DNA
<213> ORGANISM: Artificial
<220> FEATURE:
<223> OTHER INFORMATION: Synthetic oligomer for L. pneumophila 16S rRNA
      sequence
```

```
<400> SEQUENCE: 15
ctgggacggt cagataatac tggttg                                           26

<210> SEQ ID NO 16
<211> LENGTH: 25
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 16
tgggacggtc agataatact ggttg                                            25

<210> SEQ ID NO 17
<211> LENGTH: 26
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 17
gggacggtca gataatactg gttgac                                           26

<210> SEQ ID NO 18
<211> LENGTH: 23
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 18
ggacggtcag ataatactgg ttg                                              23

<210> SEQ ID NO 19
<211> LENGTH: 24
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 19
ccttcgccac tggtgttcct tccg                                             24

<210> SEQ ID NO 20
<211> LENGTH: 26
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 20
ccccacgctt tcgtgcctca gtgtca                                           26

<210> SEQ ID NO 21
<211> LENGTH: 26
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 21
```

```
ctacaatggc cgatacagag ggcggc                                        26

<210> SEQ ID NO 22
<211> LENGTH: 29
<212> TYPE: DNA
<213> ORGANISM: Artificial
<220> FEATURE:
<223> OTHER INFORMATION: Synthetic oliogmer for L. pnuemophila 16S rRNA
      sequence

<400> SEQUENCE: 22
cgtaaagggt gcgtaggtgg ttgattaag                                     29

<210> SEQ ID NO 23
<211> LENGTH: 25
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 23
gtaaagggtg cgtaggtggt tgatt                                         25

<210> SEQ ID NO 24
<211> LENGTH: 26
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 24
gattaagtta tctgtgaaat tcctgg                                        26

<210> SEQ ID NO 25
<211> LENGTH: 22
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 25
cgcgtaggaa tatgccttga ag                                            22

<210> SEQ ID NO 26
<211> LENGTH: 22
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 26
ggcctggcgc tttaagatta gc                                            22

<210> SEQ ID NO 27
<211> LENGTH: 19
<212> TYPE: RNA
<213> ORGANISM: Artificial
<220> FEATURE:
<223> OTHER INFORMATION: Synthetic oligomer for L. pneumophila 16S rRNA
      sequence

<400> SEQU cggcuaccug gccuaauac                                                19

<210> SEQ ID NO 28
<211> LENGTH: 21
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 28
gagagggtag tggaatttcc g                                             21

<210> SEQ ID NO 29
<211> LENGTH: 23
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 29
gtagagatcg gaaggaacac cag                                           23

<210> SEQ ID NO 30
<211> LENGTH: 18
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 30
tgtttgctcc ccacgctt                                                 18

<210> SEQ ID NO 31
<211> LENGTH: 45
<212> TYPE: DNA
<213> ORGANISM: Artificial
<220> FEATURE:
<223> OTHER INFORMATION: Synthetic promoter primer for 16S rRNA sequence
      of Legionella sp.
<220> FEATURE:
<221> NAME/KEY: promoter
<222> LOCATION: (1)..(27)

<400> SEQUENCE: 31
aatttaatac gactcactat agggagatgt tgctccccca cgctt                   45

<210> SEQ ID NO 32
<211> LENGTH: 25
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 32
ccagggtatc taatcctgtt tgctc                                         25

<210> SEQ ID NO 33
<211> LENGTH: 52
<212> TYPE: DNA
<213> ORGANISM: Artificial
<220> FEATURE:
<223> OTHER INFORMATION: Synthetic oligomer for 16S rRNA sequence of
      Legionella sp.
<220> FEATURE:

-continued

```
<221> NAME/KEY: promoter
<222> LOCATION: (1)..(27)

<400> SEQUENCE: 33
aatttaatac gactcactat agggagacca gggtatctaa tcctgtttgc tc       52

<210> SEQ ID NO 34
<211> LENGTH: 20
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 34
ccatgcagca cctgtatcag                                           20

<210> SEQ ID NO 35
<211> LENGTH: 47
<212> TYPE: DNA
<213> ORGANISM: Artificial
<220> FEATURE:
<223> OTHER INFORMATION: Synthetic oliogmer for 16S rRNA sequence of
      Legionella sp.
<220> FEATURE:
<221> NAME/KEY: promoter
<222> LOCATION: (1)..(27)

<400> SEQUENCE: 35
aatttaatac gactcactat agggagacca tgcagcacct gtatcag             47

<210> SEQ ID NO 36
<211> LENGTH: 18
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 36
gccatgcagc acctgtat                                             18

<210> SEQ ID NO 37
<211> LENGTH: 45
<212> TYPE: DNA
<213> ORGANISM: Artificial
<220> FEATURE:
<223> OTHER INFORMATION: Synthetic oligomer for 16S rRNA of Legionella
      sp.
<220> FEATURE:
<221> NAME/KEY: promoter
<222> LOCATION: (1)..(27)

<400> SEQUENCE: 37
aatttaatac gactcactat agggagagcc atgcagcacc tgtat               45

<210> SEQ ID NO 38
<211> LENGTH: 27
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 38
gattaaaact caaaggaatt gacgggg                                   27
```

```
<210> SEQ ID NO 39
<211> LENGTH: 18
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 39
aagcggtgga gcatgtgg                                                       18

<210> SEQ ID NO 40
<211> LENGTH: 21
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 40
ctaccctctc ccatactcga g                                                   21

<210> SEQ ID NO 41
<211> LENGTH: 48
<212> TYPE: DNA
<213> ORGANISM: Artificial
<220> FEATURE:
<223> OTHER INFORMATION: Synthetic oligomer for L. pneumophila 16S rRNA
      sequence
<220> FEATURE:
<221> NAME/KEY: promoter
<222> LOCATION: (1)..(27)

<400> SEQUENCE: 41
aatttaatac gactcactat agggagacta ccctctccca tactcgag                      48

<210> SEQ ID NO 42
<211> LENGTH: 20
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 42
gagttgcaga ctccaatccg                                                     20

<210> SEQ ID NO 43
<211> LENGTH: 47
<212> TYPE: DNA
<213> ORGANISM: Artificial
<220> FEATURE:
<223> OTHER INFORMATION: Synthetic oligomer for L. pneumophila 16S rRNA
      sequence
<220> FEATURE:
<221> NAME/KEY: promoter
<222> LOCATION: (1)..(27)

<400> SEQUENCE: 43
aatttaatac gactcactat agggagagag ttgcagactc caatccg                       47

<210> SEQ ID NO 44
<211> LENGTH: 23
<212> TYPE: DNA
<213> ORGANISM: Artificial
<220> FEATURE:
<223> OTHER INFORMATION: Synthetic oligomer for L. pneumophila 16S rRNA
      sequence
```

-continued

```
<400> SEQUENCE: 44
gagtcgagtt gcagactcca atc 23

<210> SEQ ID NO 45
<211> LENGTH: 50
<212> TYPE: DNA
<213> ORGANISM: Artificial
<220> FEATURE:
<223> OTHER INFORMATION: Synthetic oligomer for L. pneumophila 16S rRNA sequence
<220> FEATURE:
<221> NAME/KEY: promoter
<222> LOCATION: (1)..(27)

<400> SEQUENCE: 45
aatttaatac gactcactat agggagagag tcgagttgca gactccaatc 50

<210> SEQ ID NO 46
<211> LENGTH: 19
<212> TYPE: DNA
<213> ORGANISM: Artificial
<220> FEATURE:
<223> OTHER INFORMATION: Synthetic oligomer for L. pneumophila 16S rRNA sequence
<400> SEQUENCE: 46
gtaatacgga gggtgcgag 19

<210> SEQ ID NO 47
<211> LENGTH: 25
<212> TYPE: DNA
<213> ORGANISM: Artificial
<220> FEATURE:
<223> OTHER INFORMATION: Synthetic oligomer for L. pneumophila 16S rRNA sequence
<400> SEQUENCE: 47
cgccctctgt atcggccatt gtagc 25

<210> SEQ ID NO 48
<211> LENGTH: 17
<212> TYPE: DNA
<213> ORGANISM: Artificial
<220> FEATURE:
<223> OTHER INFORMATION: Synthetic oligomer for L. pneumophila 16S rRNA sequence
<400> SEQUENCE: 48
ccaggtcgcc ccttcgc 17

<210> SEQ ID NO 49
<211> LENGTH: 36
<212> TYPE: DNA
<213> ORGANISM: Artificial
<220> FEATURE:
<223> OTHER INFORMATION: Synthetic oligomer for L. pneumophila 16S rRNA sequence
<400> SEQUENCE: 49
ccaatccgga ctacgaacgg cttttgagga ttggct 36

<210> SEQ ID NO 50
<211> LENGTH: 36
<212> TYPE: DNA
<213> ORGANISM: Artificial
<220> FEATURE:
<223> OTHER INFORMATION: Synthetic oliogmer for L. pneumophila 16S rRNA
```

-continued sequence

<400> SEQUENCE: 50
ccaatccgga ctacgaccga cttttaagga tttgct        36

<210> SEQ ID NO 51
<211> LENGTH: 22
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 51
ggatgacgtc aagtcatcat gg        22

<210> SEQ ID NO 52
<211> LENGTH: 24
<212> TYPE: DNA
<213> ORGANISM: Artificial
<220> FEATURE:
<223> OTHER INFORMATION: Synthetic oligomer for L. pneumophila 16S rRNA
      sequence

<400> SEQUENCE: 52
cttacgggta gggctacaca cgtg 24

<210> SEQ ID NO 53
<211> LENGTH: 22
<212> TYPE: DNA
<213> ORGANISM: Artificial
<220> FEATURE:
<223> OTHER INFORMATION: Synthetic oligomer for L. pneumophila 16S rRNA sequence

<400> SEQUENCE: 53
gctacaccgg aaattccact ac 22

<210> SEQ ID NO 54
<211> LENGTH: 49
<212> TYPE: DNA
<213> ORGANISM: Artificial
<220> FEATURE:
<223> OTHER INFORMATION: Synthetic oligomer for L. pneumophila 16S rRNA sequence
<220> FEATURE:
<221> NAME/KEY: promoter
<222> LOCATION: (1)..(27)

<400> SEQUENCE: 54
aatttaatac gactcactat agggagagct acaccggaaa ttccactac 49

<210> SEQ ID NO 55
<211> LENGTH: 23
<212> TYPE: DNA
<213> ORGANISM: Artificial
<220> FEATURE:
<223> OTHER INFORMATION: Synthetic oligomer for L. pneumophila 16S rRNA sequence

<400> SEQUENCE: 55
cgagcgttaa tcggaattac tgg 23

<210> SEQ ID NO 56
<211> LENGTH: 22
<212> TYPE: DNA
<213> ORGANISM: Artificial

```
<220> FEATURE:
<223> OTHER INFORMATION: Synthetic oligomer for L. pneumophila 16S rRNA
      sequence

```
<210> SEQ ID NO 62
<211> LENGTH: 25
<212> TYPE: RNA
<213> ORGANISM: Artificial
<220> FEATURE:
<223> OTHER INFORMATION: Synthetic oligomer for L. pneumophila 16S rRNA
      sequence
<220> FEATURE:
<221> NAME/KEY: misc_feature
<222> LOCATION: (1)..(25)
<223> OTHER INFOR

```
<220> FEATURE:
<221> NAME/KEY: misc_feature
<222> LOCATION: (1)..(29)
<223> OTHER INFORMATION: 2' methoxy RNA nucleotides
<220> FEATURE:
<221> NAME/KEY: misc_feature
<222> LOCATION: (25)..(26)
<223> OTHER INFORMATION: C9 linker

<400> SEQUENCE: 65
cgucaaccag uauuaucuga ccgucgacg                                      29

<210> SEQ ID NO 66
<211> LENGTH: 22
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 66
gctgccgttc gacttgcatg tg                                             22

<210> SEQ ID NO 67
<211> LENGTH: 20
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 67
atcgtcgcct tggtaggccc                                                20

<210> SEQ ID NO 68
<211> LENGTH: 25
<212> TYPE: DNA
<213> ORGANISM: Artificial
<220> FEATURE:
<223> OTHER INFORMATION: Synthetic oligomer for 16S rRNA sequence of
      Legionella sp.

<400> SEQUENCE: 68
gccggtgctt cttctgtggg taacg                                          25

<210> SEQ ID NO 69
<211> LENGTH: 24
<212> TYPE: DNA
<213> ORGANISM: Artificial
<220> FEATURE:
<223> OTHER INFORMATION: Synthetic oligomer for L. pneumophila 23S rRNA
      sequence

<400> SEQUENCE: 69
cacgtgtccc ggcctacttg ttcg                                           24

<210> SEQ ID NO 70
<211> LENGTH: 51
<212> TYPE: DNA
<213> ORGANISM: Artificial
<220> FEATURE:
<223> OTHER INFORMATION: Synthetic oligomer for L. pneumophila 23S rRNA
      sequence
<220> FEATURE:
<221> NAME/KEY: promoter
<222> LOCATION: (1)..(27)

<400> SEQUENCE: 70
```

```
aatttaatac gactcactat agggagacac gtgtcccggc ctacttgttc g      51
```

<210> SEQ ID NO 71
<211> LENGTH: 29
<212> TYPE: DNA
<213> ORGANISM: Artificial
<220> FEATURE:
<223> OTHER INFORMATION: Synthetic oligomer for L. pneumophila 23S rRNA
      sequence

<400> SEQUENCE: 71

```
ctgagtaga

-continued

```
<220> FEATURE:
<223> OTHER INFORMATION: Synthetic oligomer for L. pneumophila 23S rRNA
      sequence
<220> FEATURE:
<221> NAME/KEY: promoter
<222> LOCATION: (1)..(26)

<400> SEQUENCE: 76
atttaatacg actcactata gggagactga gtagaacaat ttgggaaagt tggcg            55

<210> SEQ ID NO 77
<211> LENGTH: 54
<212> TYPE: DNA
<213> ORGANISM: Artificial
<220> FEATURE:
<223> OTHER INFORMATION: Synthetic oligomer for L. pneumophila 23S rRNA
      sequence
<220> FEATURE:
<221> NAME/KEY: promoter
<222> LOCATION: (1)..(25)

<400> SEQUENCE: 77
tttaatacga ctcactatag ggagactgag tagaacaatt tgggaaagtt ggcg             54

<210> SEQ ID NO 78
<211> LENGTH: 29
<212> TYPE: DNA
<213> ORGANISM: Artificial
<220> FEATURE:
<223> OTHER INFORMATION: Synthetic oligomer for L. pneumophila 23S rRNA
      sequence

<400> SEQUENCE: 78
gggaaagttg gcgatagagg gtgaaagcc                                         29

<210> SEQ ID NO 79
<211> LENGTH: 56
<212> TYPE: DNA
<213> ORGANISM: Artificial
<220> FEATURE:
<223> OTHER INFORMATION: Synthetic oligomer for L. pneumophila 23S rRNA
      sequence
<220> FEATURE:
<221> NAME/KEY: promoter
<222> LOCATION: (1)..(27)

<400> SEQUENCE: 79
aatttaatac gactcactat agggagaggg aaagttggcg atagagggtg aaagcc           56

<210> SEQ ID NO 80
<211> LENGTH: 31
<212> TYPE: DNA
<213> ORGANISM: Artificial
<220> FEATURE:
<223> OTHER INFORMATION: Synthetic oligomer for L. pneumophila 23S rRNA
      sequence

<400> SEQUENCE: 80
ggagcctggc gtgatttatt attgaactga g                                      31

<210> SEQ ID NO 81
<211> LENGTH: 58
<212> TYPE: DNA
<213> ORGANISM: Artificial
<220> FEATURE:
<223> OTHER INFORMATION: Synthetic oligomer for L. pneumophila 23S rRNA
      sequence
<220> FEATURE:
<221> NAME/KEY: promoter
```

<222> LOCATION: (1)..(27)

<400> SEQUENCE: 81
aatttaatac gactcactat agggagagga gcctggcgtg atttattatt gaactgag    58

<210> SEQ ID NO 82
<211> LENGTH: 57
<212> TYPE: DNA
<213> ORGANISM: Artificial
<220> FEATURE:
<223> OTHER INFORMATION: Synthetic oligomer for L. pneumophila 23S rRNA
      sequence
<220> FEATURE:
<221> NAME/KEY: promoter
<222> LOCATION: (1)..(26)

<400> SEQUENCE: 82
atttaatacg actcactata gggagaggag cctggcgtga tttattattg aactgag 57

<210> SEQ ID NO 83
<211> LENGTH: 56
<212> TYPE: DNA
<213> ORGANISM: Artificial

<220> FEATURE:
<223> OTHER INFORMATION: Synthetic oligomer for L. pneumophila 23S rRNA sequence
<220> FEATURE:
<221> NAME/KEY: promoter
<222> LOCATION: (1)..(25)

<400> SEQUENCE: 83
tttaatacga ctcactatag ggagaggagc ctggcgtgat ttattattga actgag 56

<210> SEQ ID NO 84
<211> LENGTH: 22
<212> TYPE: RNA
<213> ORGANISM: Artificial
<220> FEATURE:
<223> OTHER INFORMATION: Synthetic oligomer for L. pneumophila 23S rRNA sequence

<400> SEQUENCE: 84
cucaguucaa uaauaaauca cg 22

<210> SEQ ID NO 85
<211> LENGTH: 23
<212> TYPE: RNA
<213> ORGANISM: Artificial
<220> FEATURE:
<223> OTHER INFORMATION: Synthetic oligomer for L. pneumophila 23S rRNA sequence

<400> SEQUENCE: 85
cuuucccaaa uuguucuacu cag 23

<210> SEQ ID NO 86
<211> LENGTH: 18
<212> TYPE: RNA
<213> ORGANISM: Artificial
<220> FEATURE:
<223> OTHER INFORMATION: Synthetic oligomer for L. pneumophila 23S rRNA sequence

<400> SEQUENCE: 86
gcuccucccc guucgcuc 18

```
<210> SEQ ID NO 87
<211> LENGTH: 26
<212> TYPE: DNA
<213> ORGANISM: Artificial
<220> FEATURE:
<223> OTHER INFORMATION: Synthetic oligomer for L. pneumophila 23S rRNA sequence
<400> SEQUENCE: 87
ggauttcacg tgtcccggcc tacttg 26

<210> SEQ ID NO 88
<211> LENGTH: 24
<212> TYPE: RNA
<213> ORGANISM: Artificial
<220> FEATURE:
<223> OTHER INFORMATION: Synthetic oligomer for L. pneumophila 23S rRNA sequence
<220> FEATURE:
<221> NAME/KEY: misc_feature
<222> LOCATION: (1)..(24)
<223> OTHER INFORMATION: 2' methoxy RNA nucleotides
<220> FEATURE:
<221> NAME/KEY: misc_feature
<222> LOCATION: (5)..(6)
<223> OTHER INFORMATION: C9 linker
<400> SEQUENCE: 88
cccucaucaa accuucguag aggg 24

<210> SEQ ID NO 89
<211> LENGTH: 23
<212> TYPE: RNA
<213> ORGANISM: Artificial
<220> FEATURE:
<223> OTHER INFORMATION: Synthetic oligomer for L. pneumophila 23S rRNA sequence
<220> FEATURE:
<221> NAME/KEY: misc_feature
<222> LOCATION: (1)..(23)
<223> OTHER INFORMATION: 2' methoxy RNA nucleotides
<220> FEATURE:
<221> NAME/KEY: misc_feature
<222> LOCATION: (5)..(6)
<223> OTHER INFORMATION: C9 linker
<400> SEQUENCE: 89
cgugccuagu uccucaucgc acg 23

<210> SEQ ID NO 90
<211> LENGTH: 27
<212> TYPE: DNA
<213> ORGANISM: Artificial
<220> FEATURE:
<223> OTHER INFORMATION: Bacteriophage T7 promoter
<400> SEQUENCE: 90
aatttaatac gactcactat agggaga 27

<210> SEQ ID NO 91
<211> LENGTH: 26
<212> TYPE: DNA
<213> ORGANISM: Artificial
<220> FEATURE:
<223> OTHER INFORMATION: Bacteriophage T7 promoter
<400> SEQUENCE: 91
atttaatacg actcactata gggaga 26
```

-continued

```
<210> SEQ ID NO 92
<211> LENGTH: 25
<212> TYPE: DNA
<213> ORGANISM: Artificial
<220> FEATURE:
<223> OTHER INFORMATION: Bacteriophage T7 promoter

<400> SEQUENCE: 92
tttaatacga ctcactatag ggaga                                          25

<210> SEQ ID NO 93
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 93
accaguauua ucugaccguc cc                                             22

<210> SEQ ID NO 94
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 94
caaccaguau uaucugaccg ucc                                            23

<210> SEQ ID NO 95
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 95
caaccaguau uaucugaccg uc                                             22

<210> SEQ ID NO 96
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 96
gucaaccagu auuaucugac cguc                                           24

<210> SEQ ID NO 97
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 97
ccucaucaaa ccuucgua                                                  18

<210> SEQ ID NO 98
<211> LENGTH: 18
```

```
<212> TYPE: RNA
<213> ORGANISM: Artificial Sequence
<220> FEATURE:
<223> OTHER INFORMATION: Synthetic Oligonucleotide

<400> SEQUENCE: 98
cgugccuagu uccucauc                                                    18
```